US011364337B2

(12) United States Patent
Cabiri et al.

(10) Patent No.: US 11,364,337 B2
(45) Date of Patent: Jun. 21, 2022

(54) FORCE CONTAINMENT IN AN AUTOMATIC INJECTOR

(71) Applicant: West Pharma. Services IL, Ltd., Ra'anana (IL)

(72) Inventors: Oz Cabiri, Hod Hasharon (IL); Ran Hezkiahu, Herzliya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 316 days.

(21) Appl. No.: 16/572,024

(22) Filed: Sep. 16, 2019

(65) Prior Publication Data
US 2020/0009316 A1 Jan. 9, 2020

Related U.S. Application Data

(62) Division of application No. 16/071,574, filed as application No. PCT/US2016/068371 on Dec. 22, 2016, now Pat. No. 10,610,638.
(Continued)

(51) Int. Cl.
*A61M 5/142* (2006.01)
*A61M 5/14* (2006.01)
(Continued)

(52) U.S. Cl.
CPC ...... *A61M 5/14248* (2013.01); *A61M 5/1413* (2013.01); *A61M 5/1452* (2013.01);
(Continued)

(58) Field of Classification Search
CPC ............ A61M 5/14248; A61M 5/3287; A61M 5/1413
See application file for complete search history.

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CN | 1505535 A | 6/2004 |
| CN | 1747683 A | 3/2006 |

(Continued)

OTHER PUBLICATIONS

Int'l Search Report and Written Opinion dated May 15, 2017 in Int'l Application No. PCT/US2016/068371.
(Continued)

*Primary Examiner* — Jenna Zhang
(74) *Attorney, Agent, or Firm* — BakerHostetler

(57) ABSTRACT

An automatic injector for delivering a pharmaceutical substance from a reservoir of a cartridge, the cartridge interconnected to a needle at its distal end and mechanically coupled to a plunger driver at its proximal end, the injector comprising a connecting feature on the cartridge a contact surface for contacting an injection site a frame connected to the contact surface, the frame having an interference element with a distal stop, the interference element sized to slidably link to the connecting feature and allow the cartridge to slide up to the distal stop, a snap element allowing the interference element to receive the connection feature, but inhibiting disconnection of the cartridge; the frame further comprising a driver mount, for fixedly containing a plunger driver, the driver for driving a plunger to empty the reservoir of the cartridge through the needle to inject fluid from the reservoir into the injection subject.

10 Claims, 11 Drawing Sheets

Receiving frame

Exemplary cartridge proximal support

Related U.S. Application Data

(60) Provisional application No. 62/281,536, filed on Jan. 21, 2016.

(51) Int. Cl.

| | | |
|---|---|---|
| *A61M 5/24* | (2006.01) | |
| *A61M 5/145* | (2006.01) | |
| *A61M 5/158* | (2006.01) | |
| *A61M 5/20* | (2006.01) | |
| *A61M 5/32* | (2006.01) | |

(52) U.S. Cl.
CPC ............ *A61M 5/20* (2013.01); *A61M 5/3287* (2013.01); *A61M 2005/14252* (2013.01); *A61M 2005/14256* (2013.01); *A61M 2005/1585* (2013.01); *A61M 2005/206* (2013.01); *A61M 2005/244* (2013.01); *A61M 2005/2492* (2013.01)

(56) References Cited

U.S. PATENT DOCUMENTS

| | | |
|---|---|---|
| 1,321,550 A | 11/1919 | Platt |
| 1,704,921 A | 3/1929 | Nicoll |
| 1,795,530 A | 3/1931 | Cowan et al. |
| 1,795,630 A | 3/1931 | Wilson |
| 2,453,590 A | 11/1948 | Poux |
| 2,589,426 A | 3/1952 | Ogle |
| 2,677,373 A | 5/1954 | George |
| 2,702,547 A | 2/1955 | Glass |
| 2,860,635 A | 11/1958 | Wilburn |
| 3,203,269 A | 8/1965 | Perrine |
| 3,212,685 A | 10/1965 | James et al. |
| 3,585,439 A | 6/1971 | Schneeberger |
| 3,623,474 A | 11/1971 | Heilman et al. |
| 3,705,582 A | 12/1972 | Stumpf et al. |
| 3,708,945 A | 1/1973 | Klettke |
| 3,794,028 A | 2/1974 | Mueller et al. |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose et al. |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan et al. |
| 4,710,178 A | 12/1987 | Henri et al. |
| 4,729,208 A | 3/1988 | Galy et al. |
| 4,735,311 A | 4/1988 | Lowe et al. |
| 4,737,144 A | 4/1988 | Choksi |
| 4,772,272 A | 9/1988 | Mcfarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | Mcnaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzellner |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne et al. |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,114,406 A | 5/1992 | Gabriel et al. |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,246,670 A | 9/1993 | Haber et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A | 9/1994 | Sweeney et al. |
| 5,366,498 A | 11/1994 | Brannan et al. |
| 5,376,785 A | 12/1994 | Chin et al. |
| 5,383,865 A | 1/1995 | Michel |
| D356,150 S | 3/1995 | Duggan et al. |
| 5,415,645 A | 5/1995 | Friend et al. |
| 5,456,360 A | 10/1995 | Griffin |
| 5,478,315 A | 12/1995 | Brothers et al. |
| 5,478,316 A | 12/1995 | Bitdinger et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,609,580 A | 3/1997 | Kwiatkowski et al. |
| 5,611,785 A | 3/1997 | Mito et al. |
| 5,616,132 A | 4/1997 | Newman |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Oesterlind et al. |
| 5,690,618 A | 11/1997 | Smith et al. |
| 5,697,908 A | 12/1997 | Imbert et al. |

(56) References Cited

U.S. PATENT DOCUMENTS

| | | |
|---|---|---|
| 5,697,916 A | 12/1997 | Schraga |
| 5,725,500 A | 3/1998 | Micheler |
| 5,728,075 A | 3/1998 | Levander |
| D393,314 S | 4/1998 | Meisner et al. |
| 5,741,275 A | 4/1998 | Wyssmann |
| 5,766,186 A | 6/1998 | Faraz et al. |
| 5,776,103 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,296 A | 12/1999 | Jansen et al. |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,045,533 A | 4/2000 | Kriesel et al. |
| 6,064,797 A | 5/2000 | Crittendon et al. |
| 6,074,369 A | 6/2000 | Sage et al. |
| 6,162,197 A | 12/2000 | Mohammad |
| 6,186,979 B1 | 2/2001 | Dysarz |
| 6,186,982 B1 | 2/2001 | Gross et al. |
| 6,189,292 B1 | 2/2001 | Odell et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D461,243 S | 8/2002 | Niedospial |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,554,800 B1 | 4/2003 | Nezhadian et al. |
| 6,558,351 B1 | 5/2003 | Steil et al. |
| 6,565,541 B2 | 5/2003 | Sharp |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,685,678 B2 | 2/2004 | Evans et al. |
| 6,689,118 B2 | 2/2004 | Alchas et al. |
| 6,699,218 B2 | 3/2004 | Flaherty et al. |
| 6,719,141 B2 | 4/2004 | Heinz et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,783 B2 | 6/2004 | Hung et al. |
| 6,752,787 B1 | 6/2004 | Causey et al. |
| 6,767,336 B1 | 7/2004 | Kaplan |
| 6,768,425 B2 | 7/2004 | Flaherty et al. |
| 6,786,890 B2 | 9/2004 | Preuthun et al. |
| 6,800,071 B1 | 10/2004 | Mcconnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,907,679 B2 | 6/2005 | Yarborough et al. |
| 6,908,452 B2 | 6/2005 | Diaz et al. |
| 6,960,192 B1 | 11/2005 | Flaherty et al. |
| 6,979,316 B1 | 12/2005 | Rubin et al. |
| 6,997,727 B1 | 2/2006 | Legrady et al. |
| 7,001,360 B2 | 2/2006 | Veasey et al. |
| 7,004,104 B1 | 2/2006 | Kundus |
| 7,004,929 B2 | 2/2006 | McWethy et al. |
| 7,025,226 B2 | 4/2006 | Ramey |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,066,909 B1 | 6/2006 | Peter et al. |
| 7,094,221 B2 | 8/2006 | Veasey et al. |
| 7,097,637 B2 | 8/2006 | Triplett et al. |
| 7,112,187 B2 | 9/2006 | Karlsson |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| RE39,923 E | 11/2007 | Blom |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,326,194 B2 | 2/2008 | Zinger et al. |
| 7,344,385 B2 | 3/2008 | Chen |
| 7,364,570 B2 | 4/2008 | Gerondale et al. |
| 7,377,912 B2 | 5/2008 | Graf et al. |
| 7,390,312 B2 | 6/2008 | Barrelle |
| 7,390,314 B2 | 6/2008 | Stutz et al. |
| 7,407,493 B2 | 8/2008 | Cane |
| 7,418,880 B1 | 9/2008 | Smith |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais et al. |
| 7,488,181 B2 | 2/2009 | Van |
| 7,497,842 B2 | 3/2009 | Diaz et al. |
| 7,500,963 B2 | 3/2009 | Westbye et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | Dibiasi |
| 7,547,281 B2 | 6/2009 | Hayes et al. |
| 7,565,208 B2 | 7/2009 | Harris et al. |
| 7,569,050 B2 | 8/2009 | Moberg et al. |

(56) References Cited

U.S. PATENT DOCUMENTS

| | | |
|---|---|---|
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,611,491 B2 | 11/2009 | Pickhard |
| 7,628,770 B2 | 12/2009 | Ethelfeld |
| 7,628,772 B2 | 12/2009 | Mcconnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | Mcgrath et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Lindegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,622,966 B2 | 1/2014 | Causey et al. |
| 8,628,510 B2 | 1/2014 | Bazargan et al. |
| 8,647,303 B2 | 2/2014 | Cowe |
| 8,674,288 B2 | 3/2014 | Hanson et al. |
| 8,679,060 B2 | 3/2014 | Mernoe et al. |
| D702,834 S | 4/2014 | Norton et al. |
| 8,690,855 B2 | 4/2014 | Alderete et al. |
| 8,708,961 B2 | 4/2014 | Field et al. |
| 8,721,603 B2 | 5/2014 | Lundquist |

(56) References Cited

U.S. PATENT DOCUMENTS

| | | |
|---|---|---|
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,858,508 B2 | 10/2014 | Lavi et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe |
| 9,011,164 B2 | 4/2015 | Filman et al. |
| 9,011,387 B2 | 4/2015 | Ekman et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,138,534 B2 | 9/2015 | Yodfat et al. |
| 9,149,575 B2 | 10/2015 | Cabiri |
| 9,173,997 B2 | 11/2015 | Gross et al. |
| 9,180,248 B2 | 11/2015 | Moberg et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | Mcloughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,842,942 B2 | 11/2020 | Iibuchi et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0260233 A1 | 12/2004 | Garibotto et al. |
| 2005/0027255 A1 | 2/2005 | Lavi et al. |

(56) References Cited

U.S. PATENT DOCUMENTS

| | | |
|---|---|---|
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1* | 4/2009 | Gross ............... A61M 5/1456 604/218 |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1* | 6/2009 | De Polo ............. A61M 5/1456 604/131 |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |
| 2010/0018334 A1 | 1/2010 | Lessing |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodrat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |

(56) References Cited

U.S. PATENT DOCUMENTS

| | | |
|---|---|---|
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1* | 9/2011 | Slate ............... A61M 5/3134 604/154 |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Brüggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0118777 A1 | 5/2012 | Kakiuchi et al. |
| 2012/0123387 A1* | 5/2012 | Gonzalez ......... A61M 37/0015 604/506 |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1* | 2/2014 | Bazargan ............ A61M 5/1456 604/93.01 |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete et al. |
| 2014/0243786 A1* | 8/2014 | Gilbert ............ A61M 5/14248 604/173 |
| 2014/0261758 A1 | 9/2014 | Wlodarczyk et al. |
| 2014/0343503 A1 | 11/2014 | Holmqvist |
| 2015/0005703 A1 | 1/2015 | Hutchinson et al. |
| 2015/0073344 A1 | 3/2015 | Van Damme et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157806 A1 | 6/2015 | Knutsson |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0214637 A1 | 8/2018 | Kemp et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0175821 A1 | 6/2019 | Kamen et al. |
| 2019/0224415 A1 | 7/2019 | Dugand et al. |

(56) References Cited

U.S. PATENT DOCUMENTS

| | | | |
|---|---|---|---|
| 2019/0240417 A1 | 8/2019 | Hostettler et al. | |
| 2019/0328968 A1 | 10/2019 | Giambattista | |
| 2020/0009323 A1 | 1/2020 | Nair et al. | |
| 2020/0215270 A1 | 7/2020 | Ogawa et al. | |
| 2020/0297929 A1 | 9/2020 | Zhang | |
| 2021/0138157 A1 | 5/2021 | Bar-El et al. | |
| 2021/0220551 A1 | 7/2021 | Dowd et al. | |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 101641126 A | 2/2010 |
| CN | 201692438 U | 1/2011 |
| CN | 201941304 U | 8/2011 |
| CN | 102186733 A | 9/2011 |
| CN | 102378638 A | 3/2012 |
| CN | 105102025 A | 11/2015 |
| DE | 855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| FR | 2770136 A1 | 4/1999 |
| GB | 2436526 A | 10/2007 |
| JP | 62-112566 A | 5/1987 |
| JP | 01-172843 U | 12/1989 |
| JP | 07-194701 A | 8/1995 |
| JP | 3035448 U | 3/1997 |
| JP | 09-505758 A | 6/1997 |
| JP | 11-507260 A | 6/1999 |
| JP | 2000-107289 A | 4/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2009-502273 A | 1/2009 |
| JP | 2009-101093 A | 5/2009 |
| JP | 2010-540054 A | 12/2010 |
| JP | 2010-540156 A | 12/2010 |
| JP | 2011-136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |
| JP | 2014-518743 A | 8/2014 |
| JP | 2015-514486 A | 5/2015 |
| JP | 2016-525428 A | 8/2016 |
| JP | 2016-530016 A | 9/2016 |
| WO | 90/09202 A1 | 8/1990 |
| WO | 93/07922 A1 | 4/1993 |
| WO | 94/07553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 97/00091 A1 | 1/1997 |
| WO | 97/10012 A1 | 3/1997 |
| WO | 97/21457 A1 | 6/1997 |
| WO | 97/33638 A1 | 9/1997 |
| WO | 98/57686 A1 | 12/1998 |
| WO | 9857683 A1 | 12/1998 |
| WO | 99/29151 A1 | 6/1999 |
| WO | 99/38554 A1 | 8/1999 |
| WO | 99/59665 A1 | 11/1999 |
| WO | 00/25844 A1 | 5/2000 |
| WO | 2000069509 A1 | 11/2000 |
| WO | 01/30415 A2 | 5/2001 |
| WO | 01/30421 A2 | 5/2001 |
| WO | 01/70304 A1 | 9/2001 |
| WO | 01/72357 A2 | 10/2001 |
| WO | 01/87384 A1 | 11/2001 |
| WO | 01/89607 A2 | 11/2001 |
| WO | 01/89613 A1 | 11/2001 |
| WO | 02/02165 A2 | 1/2002 |
| WO | 02/04049 A1 | 1/2002 |
| WO | 02/34315 A1 | 5/2002 |
| WO | 02/38204 A2 | 5/2002 |
| WO | 02/56934 A2 | 7/2002 |
| WO | 02/56943 A2 | 7/2002 |
| WO | 02/72182 A1 | 9/2002 |
| WO | 03/62672 A1 | 7/2003 |
| WO | 03/90833 A1 | 11/2003 |
| WO | 2004/000397 A1 | 12/2003 |
| WO | 2004/032990 A2 | 4/2004 |
| WO | 2004/098684 A2 | 11/2004 |
| WO | 2004/105841 A1 | 12/2004 |
| WO | 2005/018703 A2 | 3/2005 |
| WO | 2005/037350 A2 | 4/2005 |
| WO | 2005/072795 A2 | 8/2005 |
| WO | 2005070485 A1 | 8/2005 |
| WO | 2006/018617 A1 | 2/2006 |
| WO | 2006/037434 A1 | 4/2006 |
| WO | 2006/052737 A1 | 5/2006 |
| WO | 2006/069380 A1 | 6/2006 |
| WO | 2006/102676 A1 | 9/2006 |
| WO | 2006/104806 A2 | 10/2006 |
| WO | 2006/121921 A2 | 11/2006 |

(56) References Cited

FOREIGN PATENT DOCUMENTS

| WO | 2007/017052 A1 | 2/2007 |
| --- | --- | --- |
| WO | 2007/051563 A1 | 5/2007 |
| WO | 2007/056504 A1 | 5/2007 |
| WO | 2007/066152 A2 | 6/2007 |
| WO | 2007/073228 A1 | 6/2007 |
| WO | 2007/119178 A2 | 10/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009/022132 A2 | 2/2009 |
| WO | 2009/043564 A1 | 4/2009 |
| WO | 2009/044401 A2 | 4/2009 |
| WO | 2009/046989 A2 | 4/2009 |
| WO | 2009043000 A1 | 4/2009 |
| WO | 2009/069064 A1 | 6/2009 |
| WO | 2009/125398 A2 | 10/2009 |
| WO | 2009/144085 A2 | 12/2009 |
| WO | 2010/078227 A1 | 7/2010 |
| WO | 2010/078242 A1 | 7/2010 |
| WO | 2010/089313 A1 | 8/2010 |
| WO | 2011/075105 A1 | 6/2011 |
| WO | 2011/090955 A1 | 7/2011 |
| WO | 2011/090956 A2 | 7/2011 |
| WO | WO 2011/101378 A1 | 8/2011 |
| WO | 2011110872 A1 | 9/2011 |
| WO | 2011/124631 A1 | 10/2011 |
| WO | 2011/129175 A1 | 10/2011 |
| WO | 2011/131778 A1 | 10/2011 |
| WO | 2011/131780 A2 | 10/2011 |
| WO | 2011/131781 A1 | 10/2011 |
| WO | 2011/133823 A1 | 10/2011 |
| WO | 2011/156373 A1 | 12/2011 |
| WO | 2012/003221 A1 | 1/2012 |
| WO | 2012/032411 A2 | 3/2012 |
| WO | 2012/040528 A1 | 3/2012 |
| WO | 2012/145752 A2 | 10/2012 |
| WO | 2012/160157 A1 | 11/2012 |
| WO | 2012/168691 A1 | 12/2012 |
| WO | 2013036602 A1 | 3/2013 |
| WO | 2013/058697 A1 | 4/2013 |
| WO | 2013/115843 A1 | 8/2013 |
| WO | 2014/132293 A1 | 9/2014 |
| WO | 2014/179117 A1 | 11/2014 |
| WO | 2014/179774 A1 | 11/2014 |
| WO | 2014/194183 A2 | 12/2014 |
| WO | 2015/048791 A1 | 4/2015 |
| WO | 2015/048803 A2 | 4/2015 |
| WO | 2015/078868 A1 | 6/2015 |
| WO | 2015/091758 A1 | 6/2015 |
| WO | 2015/091850 A1 | 6/2015 |
| WO | 2015/114158 A1 | 8/2015 |
| WO | 2015/114428 A1 | 8/2015 |
| WO | 2015/118358 A1 | 8/2015 |
| WO | 2015/163009 A1 | 10/2015 |
| WO | 2016087626 A1 | 6/2016 |
| WO | 2016087627 A1 | 6/2016 |
| WO | 2016/141082 A1 | 9/2016 |
| WO | 2017/022639 A1 | 2/2017 |
| WO | 2017/161076 A1 | 9/2017 |
| WO | 2018/222521 A1 | 12/2018 |
| WO | 2019/224782 A1 | 11/2019 |
| WO | 2020/120087 A1 | 6/2020 |
| WO | 2020/193468 A1 | 10/2020 |

OTHER PUBLICATIONS

Int'l Preliminary Report on Patentability dated Nov. 22, 2017 in Int'l Application No. PCT/US2016/068371.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated Mar. 5, 2014 in CN Application No. 200880117084.X.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.

(56) References Cited

OTHER PUBLICATIONS

Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Office Action dated Feb. 20, 2015 in U.S. Appl. No. 13/521.181 by Cabiri.
Office Action dated Nov. 6, 2015 in U.S. Appl. No. 14/715,791 by Cabiri.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
Inte'l Search Report and Written Opinion dated Nov. 30, 2016 in Int'l Application No. PCT/US2016/056223.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Offce Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 30, 2013 in CN Application No. 200880117084.X.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.
Office Action dated Jun. 9, 2017 in EP Application No. 14166591.9.
Office Action dated Jun. 9,2 017 in EP Application No. 14166596.8.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.

(56) References Cited

OTHER PUBLICATIONS

U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab- le-syringe-system, Download date: Jan. 2009, original posting date: Jun. 2008, 2 pages.
Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.
European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.
Extended Search Report dated Aug. 7, 2014 in EP Application No. 14171477.4.
Extended Search Report dated Jul. 7, 2017 in EP Application No. 16193157.1.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Mar. 27, 2017 in Int'l Application No. PCT/US2016/056247.
Int'l Search Report and Written Opinion dated Apr. 21, 2017 in Int'l Application No. PCT/US2016/068367.
Int'l Search Report and Written Opinion dated Jul. 6, 2017 in Int'l Application No. PCT/US2017/022966.
Int'l Search Report and Written Opinion dated Nov. 28, 2016 in Int'l Application No. PCT/US2016/056218.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Inl'l Application No. PCT/US2016/056227.
Int'l Search Report and Written Opinion dated Dec. 15, 2016 in Inl'l Application No. PCT/US2016/056258.
Int'l Search Repport (Partial), dated Dec. 20, 2016 in Int'l Application No. PCT/US2016/056247.
Int'l Preliminary Report on Patentability dated Jan. 8, 2018 in Int'l Application No. POT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.

\* cited by examiner

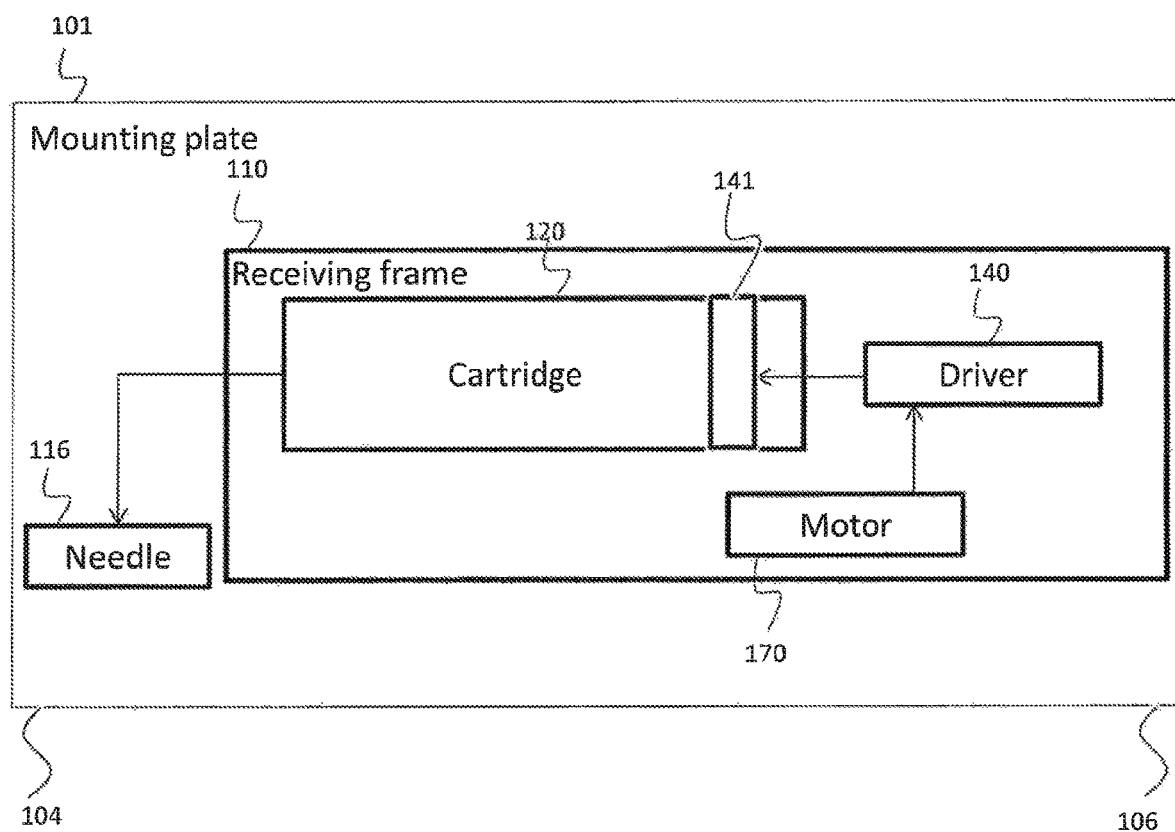
FIG. 1 Block diagram

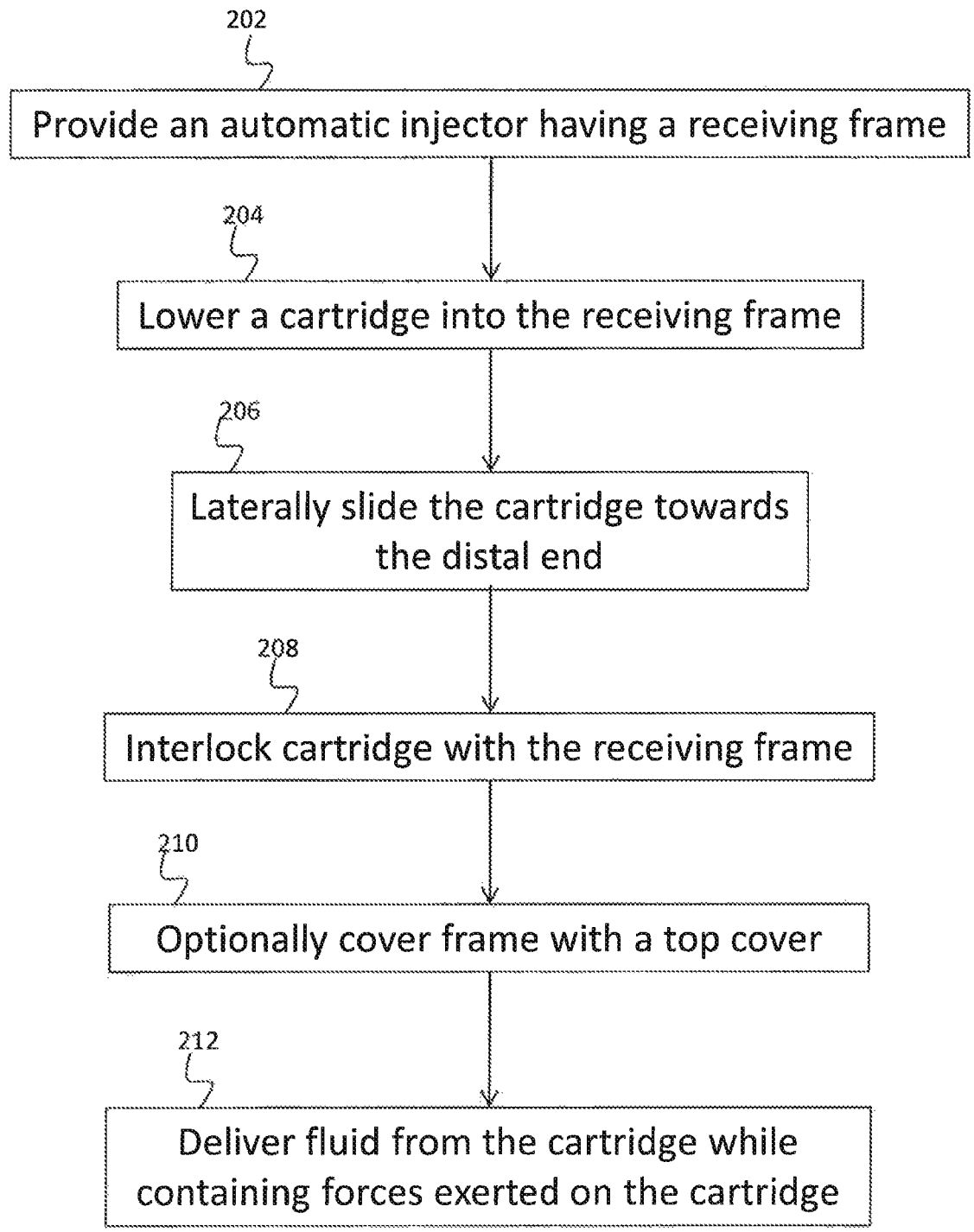
FIG. 2 high level overview

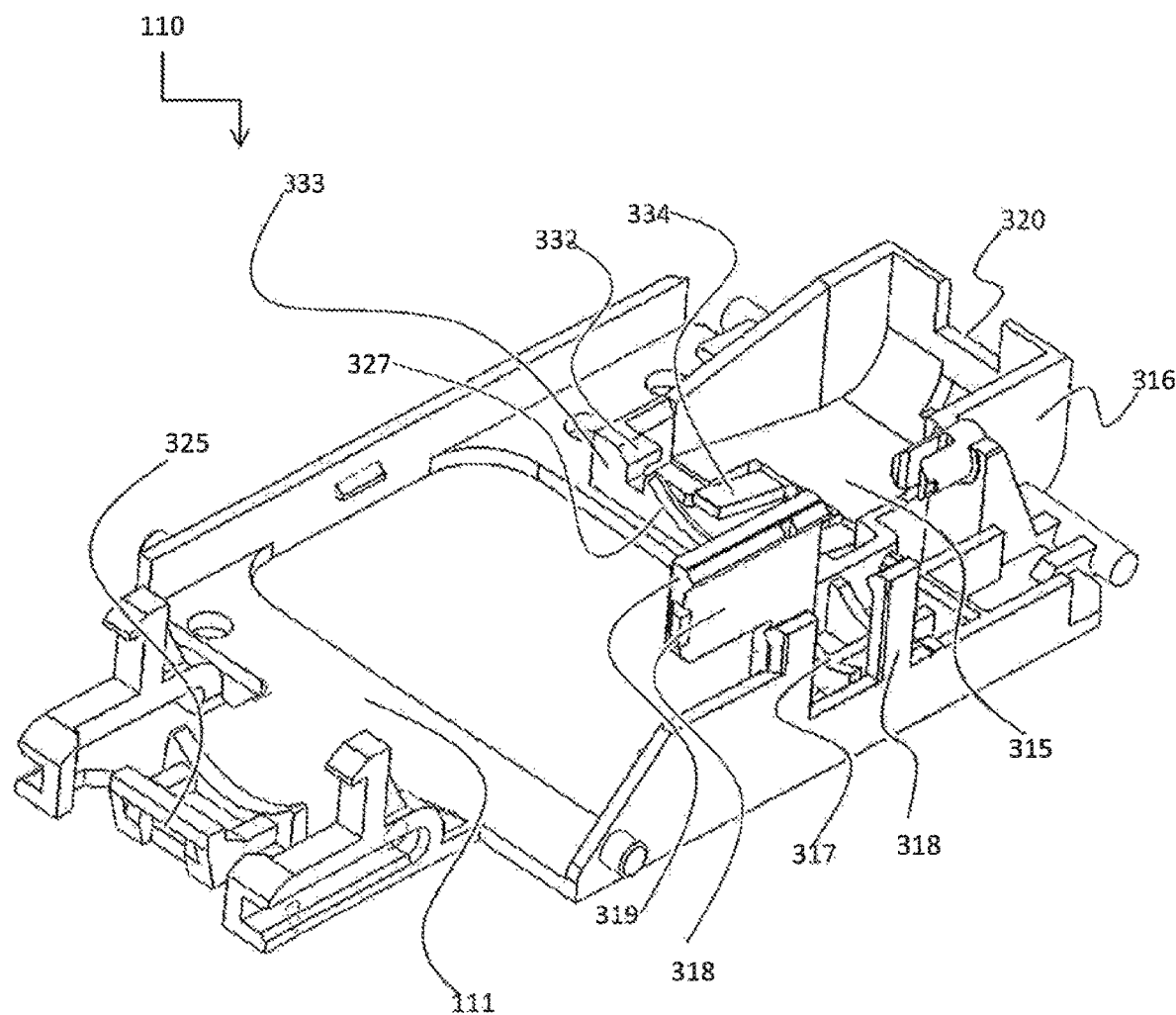
FIG. 3A Receiving frame

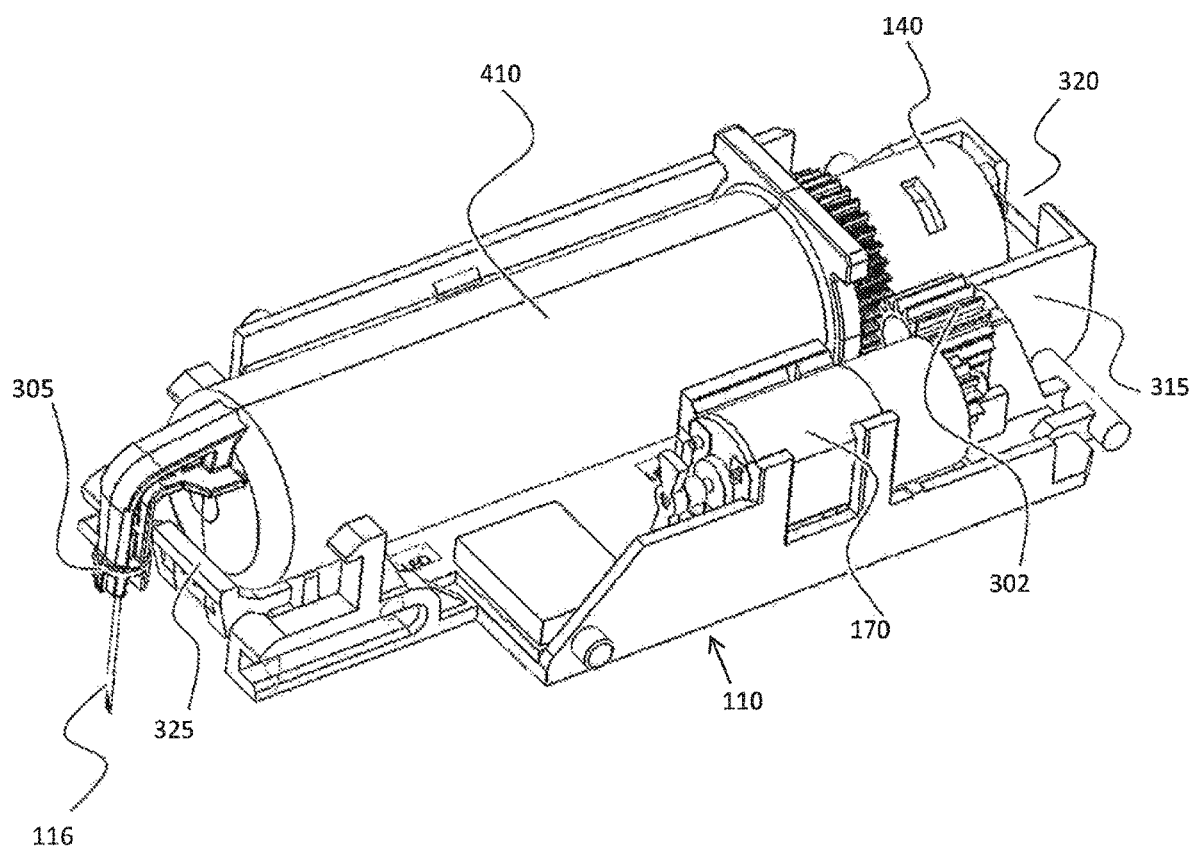
FIG. 3B Exemplary receiving frame components support

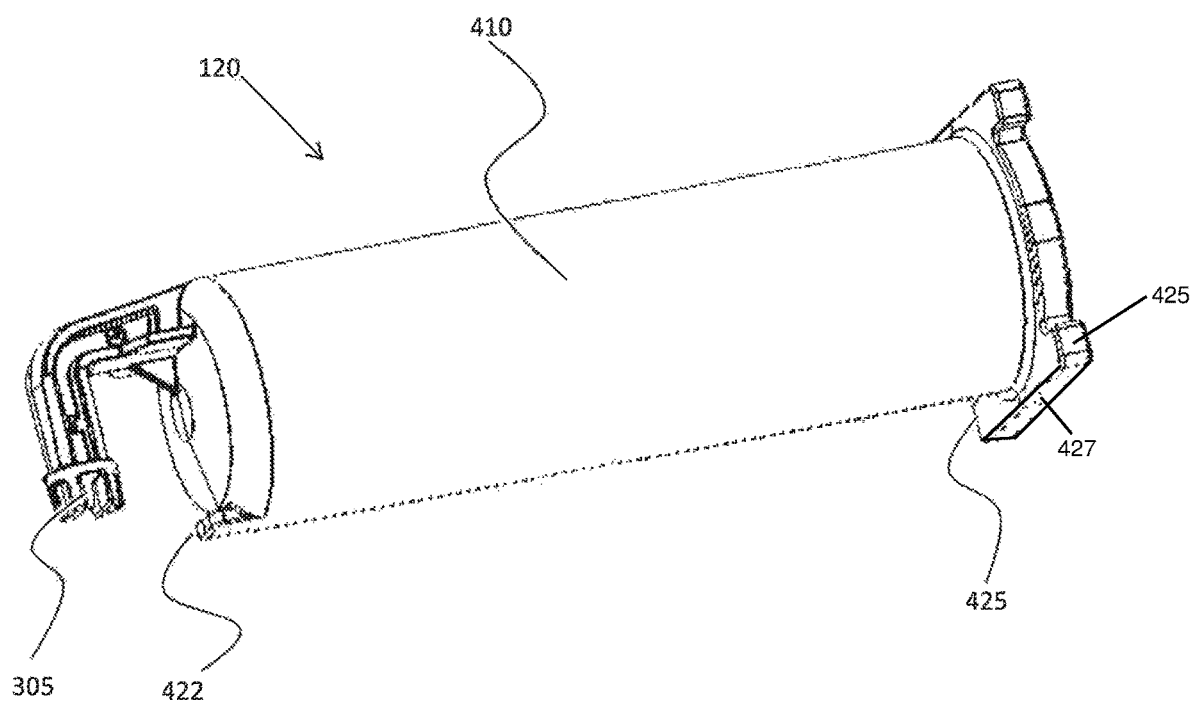
FIG. 4 Exemplary cartridge with fitting geometry

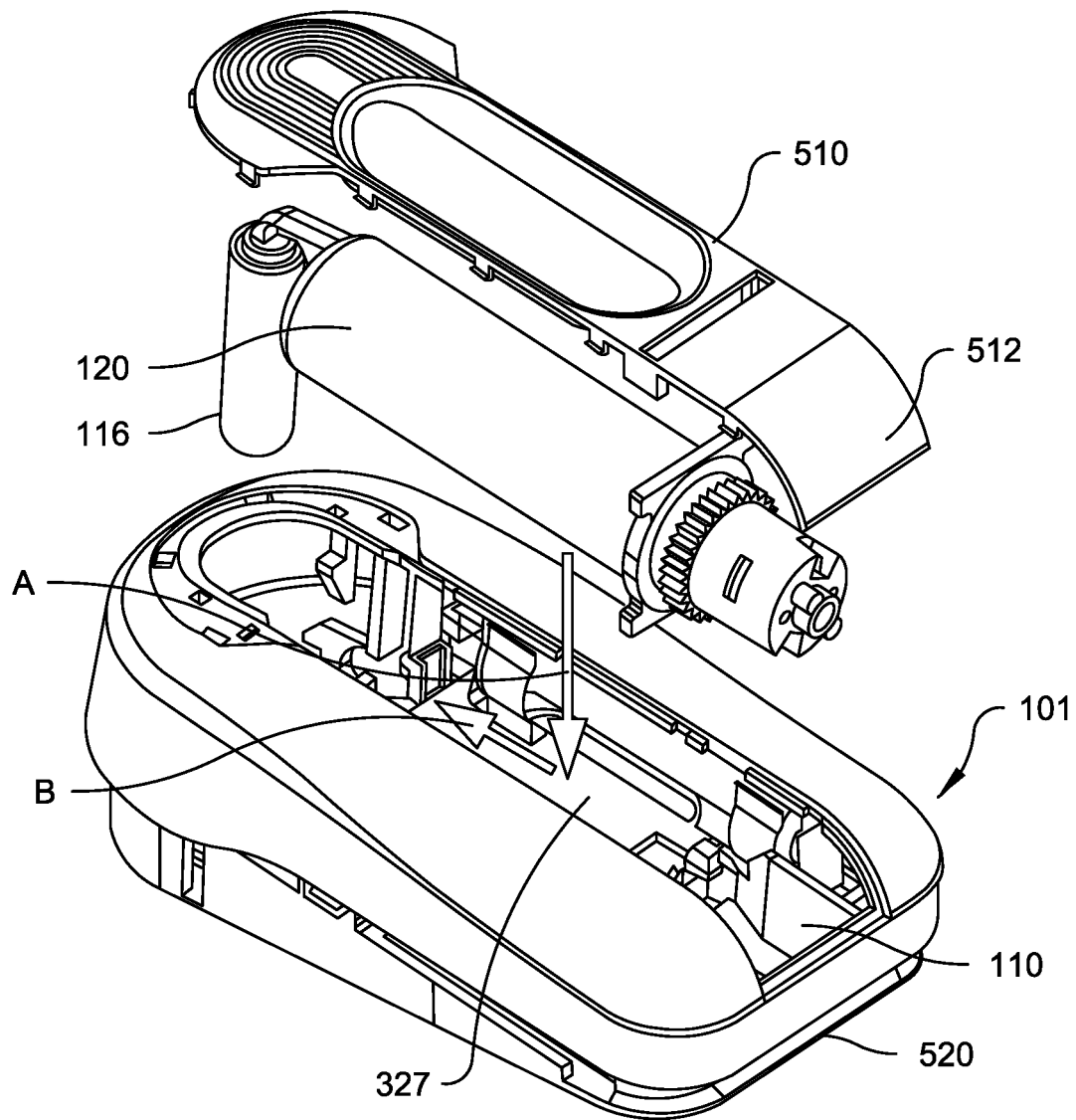
FIG. 5 Exemplary assembly

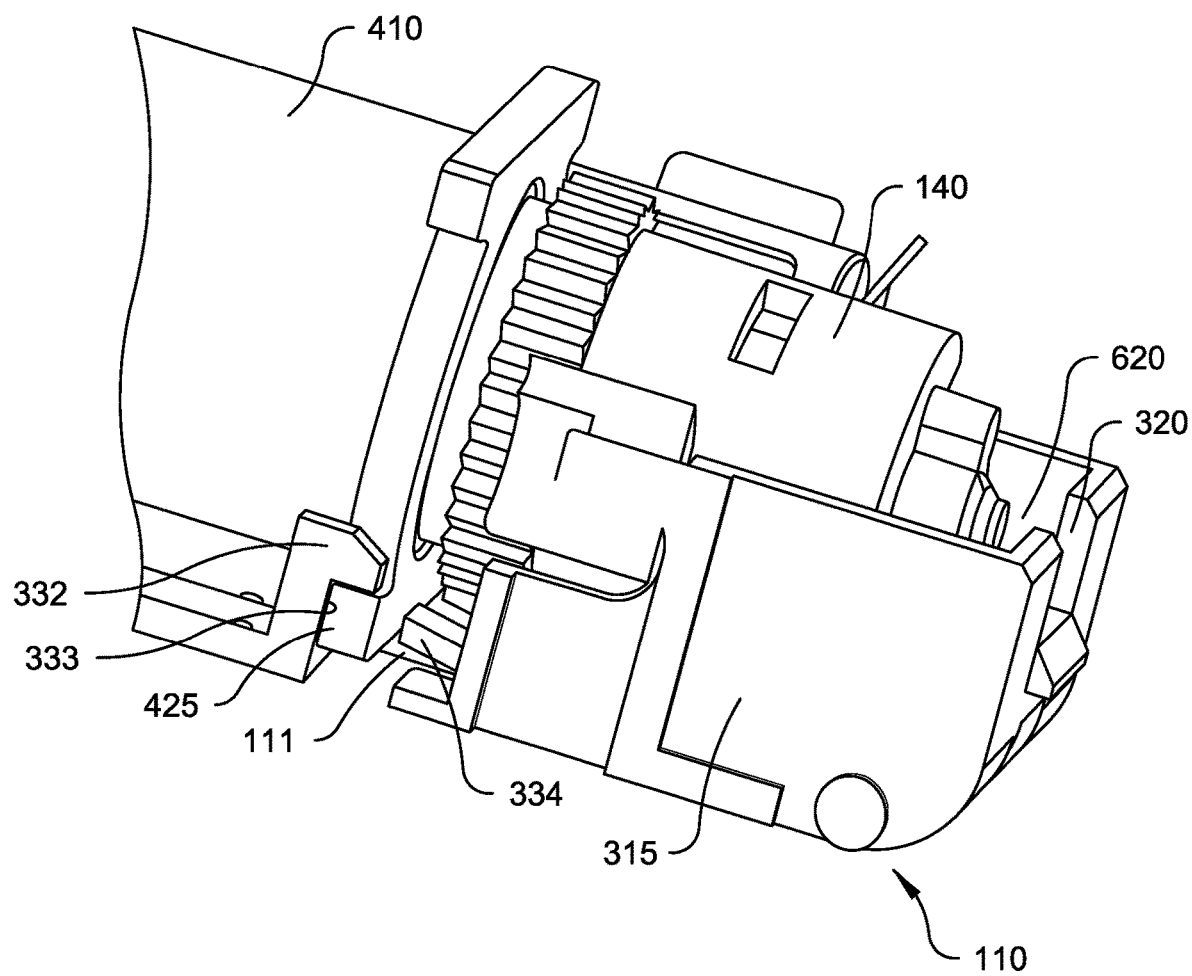
FIG. 6 Exemplary cartridge proximal support

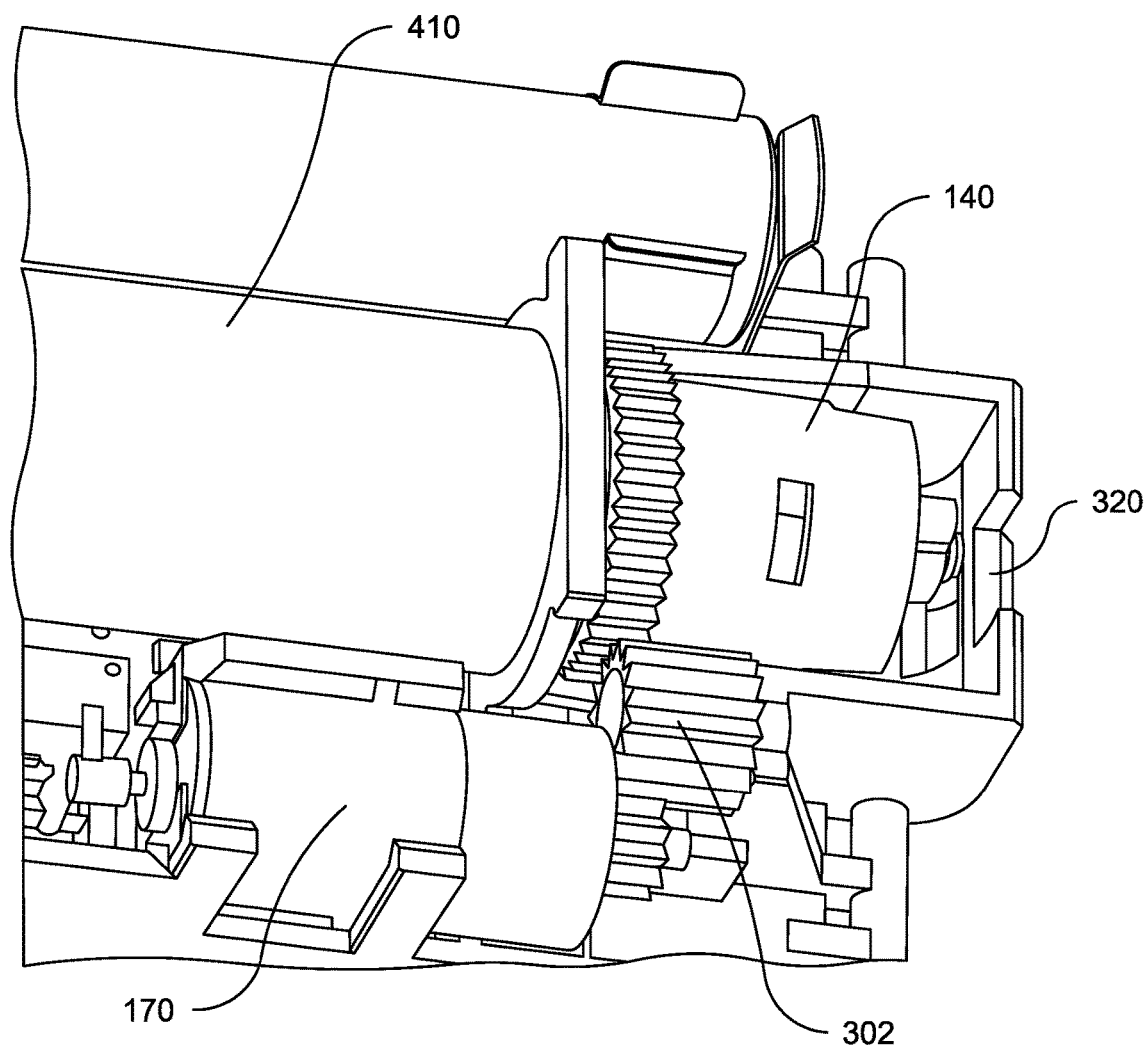
FIG 7 Exemplary receiving frame components proximal support

FIGs. 8A-B Exemplary cartridge snap

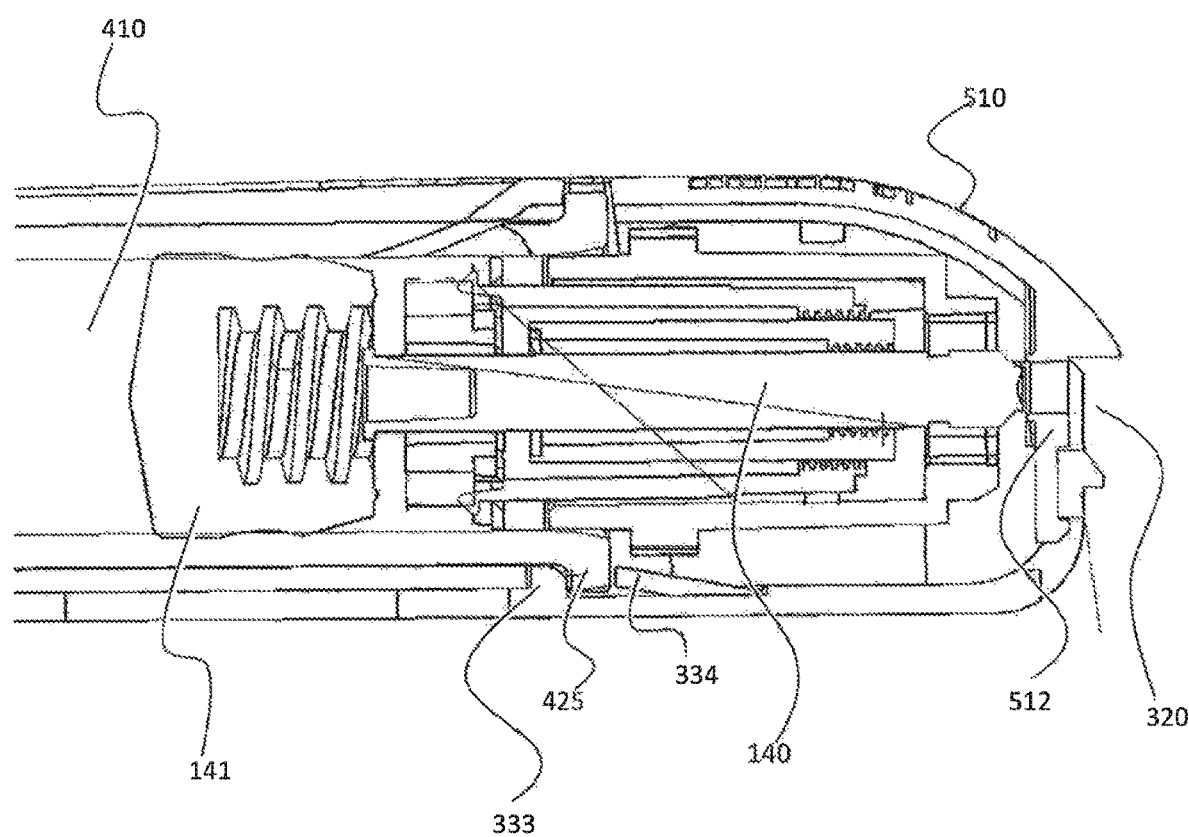
FIG. 9 Exemplary cover support

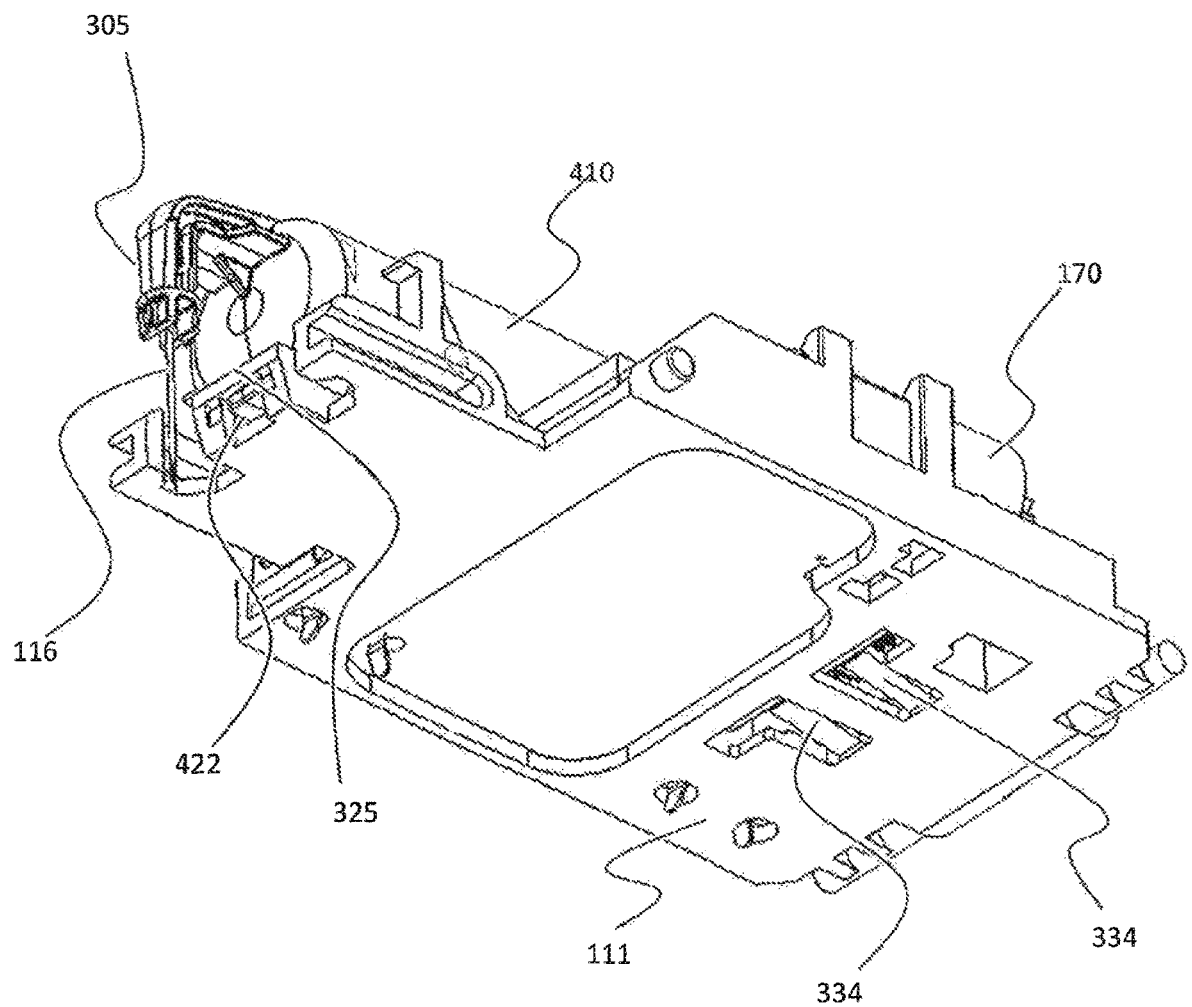
FIG. 10 Receiving frame and cartridge distal end

FORCE CONTAINMENT IN AN AUTOMATIC INJECTOR

RELATED APPLICATION

This application is a divisional application of similarly-titled, co-pending U.S. application Ser. No. 16/071,574, filed Jul. 20, 2018, which is a section 371 of International Application No. PCT/US16/68371, filed Dec. 22, 2016, which was published in the English language on Jul. 27, 2017 under International Publication No. WO 2017/127216 A1, which claims the benefit of U.S. Provisional Application No. 62/281,536, filed Jan. 21, 2016, the disclosures of each which are incorporated herein by reference in their entirety.

FIELD AND BACKGROUND OF THE INVENTION

The present invention, in some embodiments thereof, relates to automatic injectors and, more particularly, but not exclusively, to force containment in automatic injectors.

U.S. Pat. Nos. 6,500,150, 6,824,529, and 6,843,782 disclose a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject.

For such relatively slow release, an automatic expulsion device has also been suggested. U.S. Pat. No. 5,858,001 discloses a liquid drug delivery device adhered to the skin of a subject by a base member defining a skin-contacting surface having an adhesive coating. A columnar cartridge serves as reservoir for the drug and is incorporated in a housing which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

Additional background art includes U.S. Pat. No. 6,189,292. U.S. Patent Publication No. 20130253434, U.S. Patent Publication No. 2009/0093792, U.S. Pat. No. 7,967,795.

SUMMARY OF THE INVENTION

Example 1

An automatic injector for delivering a pharmaceutical substance from a reservoir of a cartridge, the cartridge interconnected to a needle at its distal end and mechanically coupled to a plunger driver at its proximal end, the injector comprising a connecting feature on the cartridge; a contact surface for contacting an injection site a frame connected to the contact surface, the frame having: an interference element with a distal stop, the interference element sized to slidably link to the connecting feature and allow the cartridge to slide up to the distal stop, a snap element allowing the interference element to receive the connection feature, but inhibiting disconnection of the cartridge; the frame further comprising a driver mount, for fixedly containing a plunger driver, the driver for driving a plunger to empty the reservoir of the cartridge through the needle to inject fluid from the reservoir into the injection subject.

Example 2

The automatic injector of example 1, wherein the frame is unitary.

Example 3

The automatic injector of example 1, wherein the frame comprises a motor mount, for fixedly containing a motor in operable communication with the plunger driver.

Example 4

The automatic injector of example 3, wherein the motor, the driver and the reservoir having longitudinal axes positioned on the same plane.

Example 5

The automatic injector of example 1, wherein the frame is positioned in a proximal portion of the housing.

Example 6

The automatic injector of example 1, wherein the frame is suitable for reducing translational movement of the cartridge.

Example 7

The automatic injector of example 1, wherein the frame is suitable for reducing rotational movement of the cartridge.

Example 8

The automatic injector of example 1, wherein the driver mount comprises a walled container having a top opening.

Example 9

The automatic injector of example 8, further comprising a top cover having at least one extension complementing at least one gap in the walled container.

Example 10

The automatic injector of example 9, wherein the top cover comprises an extension sized to fit between a gap in a proximal wall of the walled container and a proximal portion of the plunger driver, once the plunger driver slides in a distal direction.

Example 11

A receiving frame for immobilizing a cartridge having a connection feature to an automatic injector housing, the cartridge having a needle at its distal end, and is mechanically coupled in its proximal end to a plunger driver, comprising a ventral side for fitting into a base portion of the automatic injector; and a dorsal side having: a cartridge mount for receiving the cartridge from above, the cartridge mount comprises a interference element with a distal stop, the interference element sized to slidably link to the connection feature and allow the cartridge to slide up to the distal stop, and a snap element allowing the interference element to receive the connection feature, but inhibiting disconnection of the cartridge; and a driver mount, for fixedly containing the plunger driver, the driver mount comprising a walled container sized to at least partially surround the plunger driver and having an open top for receiving the plunger driver from above; wherein the cartridge and the driver are mechanically coupled through the plunger.

Example 12

The receiving frame of example 11, further comprising a motor mount, for fixedly containing a motor in operable communication with the plunger driver, the motor mount comprising a walled container sized to at least partially surround the motor and having an open top for receiving the motor from above;

Example 13

The receiving frame of example 11, wherein the cartridge mount, the driver mount and the motor mount are made of a unitary piece.

Example 14

The receiving frame of example 11, wherein longitudinal axes of the cartridge, the plunger driver and the motor are positioned on the same plane.

Example 15

The receiving frame of example 11, wherein the driver mount contains forces of at least 20 Kg*cm.

Example 16

The receiving frame of example 11, wherein the interference fit is shaped to surround a portion of the cartridge from a dorsal, a distal and a ventral side of the cartridge portion.

Example 17

A method of connecting a cartridge having a connection feature to an automatic injector having a motor, the cartridge interconnected to a needle at its distal end and mechanically coupled to a plunger driver at its proximal end, comprising lowering the cartridge while being mechanically coupled with the plunger driver into a receiving frame of the automatic injector, the receiving frame having an open top; sliding the cartridge in a direction of the distal end until reaching a distal stop; linking the connection feature to an interference element of the receiving frame; snapping the connection feature, such that disconnection of the cartridge is inhibited; and containing forces generated by the plunger driver on the cartridge through the receiving frame, thereby immobilizing the cartridge with respect to the automatic injector.

Example 18

The method of example 17, wherein the containing forces comprises mechanically interfering with an axial translation of the cartridge.

Example 19

The method of example 17, wherein the containing forces comprises mechanically interfering with a rotational translation of the cartridge.

Example 20

The method of example 17, wherein the interlocking comprises surrounding a portion of the cartridge from at least four directions being a dorsal side, a ventral side, a proximal side and a distal side.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a block diagram schematically representing an automatic injector receiving frame for fitting with a cartridge and a driving system of the cartridge, in accordance with some embodiments of the invention;

FIG. 2 is a high level overview of a method for immobilizing movement of a cartridge with respect to an automatic injector assembly, in accordance with some embodiments of the invention;

FIG. 3A is an exemplary unitary receiving frame illustrating a distal and proximal geometry for fitting with and immobilizing components of an automatic injector, in accordance with some embodiments of the invention;

FIG. 3B is an exemplary unitary receiving frame fitted with various components of an automatic injector, in accordance with some embodiments of the invention;

FIG. 4 is an exemplary cartridge having distal and proximal mounting pins for connecting with a receiving frame, in accordance with some embodiments of the invention;

FIG. 5 is an explosive view of an automatic injector being loaded with a cartridge and covered with a cover, in accordance with some embodiments of the invention;

FIG. 6 is a close-up cross-sectional view of an exemplary geometry and interference connection of a proximal portion of a unitary receiving frame with a proximal portion of a cartridge, in accordance with some embodiments of the invention;

FIG. 7 is a perspective top view of an exemplary side-by-side configuration of the cartridge and the driving system of the cartridge, in accordance with some embodiments of the invention;

FIGS. 8A and 8B illustrate a side view of a snap fitting and immobilization of a cartridge, in accordance with some embodiments of the invention, wherein FIG. 8A illustrates a cross-sectional view of FIG. 8B illustrates a partial perspective view;

FIG. 9 is a cross-sectional side view of the automatic injector, illustrating an incorporation of a cover extension in the immobilization system, in accordance with some embodiments of the invention; and FIG. 10 illustrates a bottom perspective view of an exemplary unitary receiving frame, showing a distal fitting with a cartridge, in accordance with some embodiments of the invention.

DESCRIPTION OF SPECIFIC EMBODIMENTS OF THE INVENTION

Figure 8A:
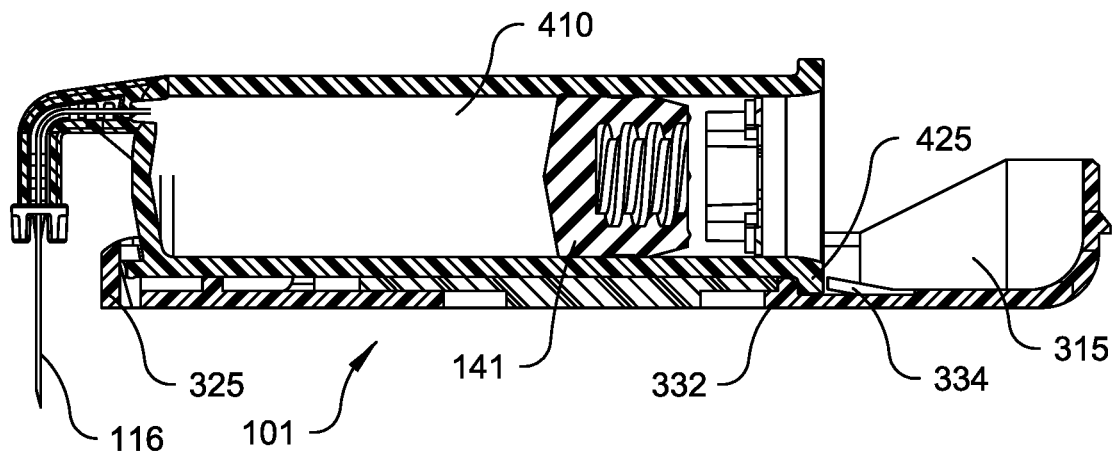

The present invention, in some embodiments thereof, relates to automatic injectors and, more particularly, but not exclusively, to force containment in automatic injectors.

Overview

An aspect of several embodiments of the invention relates to immobilizing a cartridge with respect to an automatic injector mounting plate, the mounting plate used for mounting over an injection subject. In some embodiments, immobilizing includes reducing axial translation of the cartridge, for example, axial translation of the cartridge towards the distal end of the mounting plate, defined as the end comprising an injection needle, and/or axial translation of the cartridge towards the proximal end of the mounting plate, defined as the end comprising a plunger. Alternatively or additionally, immobilizing comprises inhibiting rotational movement of the cartridge, for example, movement in the form of rotation around the longitudinal axis of the cartridge.

In some embodiments, it is desirable that the cartridge is immobilized in the injector sufficiently that operating the plunger mechanism to expel the contents does not move the cartridge. If the cartridge were to move then the needle may cause discomfort to the patient in the skin around the needle. This is especially relevant for a cartridge having a bent fluid path, which translates any rotational movement of the cartridge into an axial translation movement of the elongated axis of the needle.

In order to provide such immobilization, in some embodiments, a receiving frame is provided within the injector mounting plate to receive the cartridge. Optionally, the cartridge is fixedly received, i.e. while the cartridge is received it is also fixed to the receiving frame. For example, fixed includes immobilizing movement of more than 0.1 mm, and/or more than 0.5 mm, and/or more than 1 mm, and/or more than 2 mm, and/or more than 4 mm. In some embodiments, the receiving frame engages the cartridge such that forces exerted on the cartridge, forces which might cause its translation and/or rotation, are sufficiently reduced. Alternatively or additionally, the receiving frame is provided to contain force generated by components which are mechanically coupled to the cartridge. In some embodiments, the cartridge is mechanically coupled to a plunger driver, optionally by having a driving system which is mechanically connected to a plunger residing within the reservoir of the cartridge. In some embodiments, the plunger driver is found in a mechanical operable communication with a motor, optionally through a transmission system. Optionally, forces generated by the motor, and/or by the plunger driver are contained within the receiving frame. In some embodiments, a single frame is used for fixedly receiving the cartridge and its associated plunger driver and/or motor.

Optionally, the receiving frame is formed as a unitary frame. As used herein, unitary includes being formed and/or molded as a single unit, without having more than one component. It should be noted that having a plurality of components being interlocked to form a single unit, are not included herein in the scope of the term unitary. In order to avoid movement of the distal portion of the cartridge, where the needle is positioned, it is preferable to dissipate forces near their source, e.g. the proximal portion comprising the motor and driving system. Alternatively or additionally, it is useful to utilize a receiving frame having as little as possible different parts, such as no more than three, or no more than two, or no more than one unitary frame.

In some embodiments, the receiving frame comprises a dorsal side for fixedly receiving at least the cartridge, and a ventral side for placing onto a mounting plate. Optionally, the receiving frame is hingely connected to the mounting plate, optionally at its sides. In some embodiments, it is desirable that the injector housing would have a small height, potentially enabling easier gripping. In some embodiments, the height may be reduced by positioning of the cartridge, the driver mount and the motor in a side-by-side arrangement, for example by positioning the longitudinal axes of each of the cartridge, the plunger driver and the motor on the same plane, optionally, parallel to the plane defined by the base of the housing, and/or the plane used for mounting on the injection subject.

In some embodiments, the receiving frame comprises at least one interference element which has a geometry for holding the cartridge. In some embodiments, the interference element engages with a connection feature, such as for example a complementary geometry, comprised in the cartridge. For example, the interference element may include holders into which complementary geometry in the form of extensions on the body of the cartridge can slide into. In some embodiments, the cartridge and its complementary geometry slide towards the distal end of the housing, up to a distal stop. Optionally, the complementary geometry is then latched at a final resting position by a catch located behind, so that the cartridge can be inserted with a down, slide and click operation. As used herein, an interference element includes a restraining geometry for engaging with a connection feature of the cartridge, for example, by enveloping the connection feature from three directions, or being enveloped by the connection feature in three directions.

Alternatively or additionally, the cartridge may include a complementary geometry in the form of flange and/or cut out and/or bevel and/or an indentation and/or a protrusion and/or a pin and/or a stabilizer and/or a hole and/or a snap fitting and/or hook and/or a pin designed to mate with the fitting of the interference element of the receiving frame. Optionally, the interference element includes a flange and/or cut out and/or bevel and/or an indentation and/or a protrusion and/or a pin and/or a stabilizer and/or a hole and/or a snap fitting and/or hook and/or a pin.

In some embodiments, a non-symmetric cartridge is provided. Optionally, loading the non-symmetric syringe into a device in the correct orientation requires reference points and/or connection features. In some embodiments, the fitted geometry of the interference elements with the complementary geometry of the cartridge serves as reference points.

In some embodiments, interference elements are sized and shaped to accommodate three sides of the complementary geometry, optionally the dorsal side, the ventral side and the distal side, resulting in a holder which holds the complementary geometry in three directions. Alternatively, it is the complementary geometry which surrounds the interference element, optionally across the dorsal side, the ventral side and the proximal side. In some embodiments, mechanically interfering across the dorsal and ventral portions of the complementary elements mechanically hinders their movement. In some embodiments, at least two interference elements are provided in opposite locations positions along the longitudinal axis of the cartridge, each positioned at an opposite location across the cartridge reservoir. Potentially, providing mechanical interference in at least two locations positioned across the circular diameter of the cartridge reduces rotational movement.

In some embodiments, after the cartridge slides to be engaged with the interference elements, up to the distal stop, an elastic element closes a fourth side of the cartridge. For example, a snap may be elastically pushed down when lowering the cartridge into the receiving frame, and once the cartridge slides towards the distal end, the elastic element is released and secures the cartridge from a fourth side, such as the proximal side. Optionally, the elastic element is a snap. In some embodiments, at least two snaps are provided, each securing an engagement of at least two interference elements with complementary geometries. In some embodiments, securing the complementary geometry of the cartridge from the distal end, such as by the distal stop, and from the proximal end, such as by the elastic element, reduces movement in a lateral, axial translocation.

In some embodiments, the receiving frame is configured to hold the proximal side of the cartridge and the plunger driver together. In some embodiments, the walled driver mount balances rearward forces of the plunger driver while the interference elements balance longitudinal forces between the plunger driver and the cartridge. In some embodiments, torque formed between the transmission, the plunger driver and the cartridge is directed to the proximal portion of the receiving frame. In some embodiments, the interference elements and the walled containments prevent movement in a distal direction, in an upwards direction or in a rotation around the axis of the cartridge. In some embodiments, the proximal elastic element prevents the cartridge from moving proximally and also prevents the cartridge from being disconnected from the receiving frame.

In some embodiments, the receiving frame comprises a distal complementary element for engaging and stabilizing a distal portion of the cartridge near the needle. In some embodiments, the cartridge comprises a bent fluid path extending from a dorsal outlet and bending towards the ventral side of the cartridge. In some embodiments, the distal complementary element is positioned on the free ventral side of the cartridge. In some embodiments, when the distal complementary element is engaged with the receiving frame, forces emanating from the needle, such as from usage of the needle or from delivery shocks, are dissipated. For example, a distal portion of a cartridge might have has an elongated protrusion, extending beyond the edge of the cartridge, and being complementary to slide into a hole provided in the receiving frame. In some embodiments, distal connectors hold the needle steady against vertical forces of needle insertion or lateral forces against the needle. In some embodiments, the fitting geometry also prevents forward movement in the axial direction. In some embodiments, the distal pin is within the cross section of the cartridge and does not interfere with a process for filling the cartridge.

In some embodiments, the cartridge itself comprises complementary geometry elements for fitting with geometric elements in the receiving frame. In some embodiments, a cross-section across a reservoir of the cartridge lacks an axial symmetry, for example, it is not round. Alternatively or additionally, the cross-section across a reservoir of the cartridge has a central symmetry, for example, by having a geometrical element on either side of the reservoir. In some embodiments, the cartridge is manufactured by molding, optionally Crystal Zenith. A potential advantage of molding is the possibility to build into the cartridge geometric features which make the syringe easier to mount in an injection device. Alternatively or additionally, the syringe may include a molded component. Optionally the molded component includes the extension. For example the molded component may be made of Daikyo Resin CZ (Crystal Zenith) or other Cyclic Olefin Polymer (COP) or any moldable material suitable to use with drug product. Alternatively or additionally, molded components may be made of, for example, polycarbonate and/or polypropylene and/or other polymers.

An aspect of some embodiments of the invention relates to a receiving frame to be fit within of an automatic injector, optionally within a proximal portion, and for containing forces generated between a motor, a plunger driver and a cartridge comprising the plunger. In some embodiments, a unitary frame is provided having at least two mount containments, one for each of the plunger driver and the cartridge. In some embodiments, the unitary frame is further provided with a third mount containment for the motor. Optionally, the unitary frame comprises walls for containing and dissipating the forces emanating from each of the motor and/or the plunger driver.

In some embodiments, the receiving frame is configured to receive from above a cartridge being mechanically coupled to the plunger driver. Optionally, the cartridge is mechanically coupled to the plunger driver through a plunger which resides within the reservoir of the cartridge and is mechanically connected to at least one arm of the plunger driver. In some embodiments, the plunger driver comprises a driving assembly, optionally a telescopic system. For example, the plunger driver may include threaded telescoping rods such that when a transmission is rotated (for example by a motor) the telescoping rods expand the plunger into the reservoir possibly causing discharge of a pharmaceutical substance out of the cartridge fluid path.

Alternatively, the receiving frame is configured to receive from above a cartridge being mechanically coupled to the plunger driver and to the motor, for example, through a transmission mechanically coupling an operative communication between the motor and the plunger driver.

In some embodiments, the mount containments of the receiving frame comprise an open top, allowing the lowering of the cartridge and its associated components into the receiving frame from above. In some embodiments, the geometry of the receiving frame is configured to allow lateral sliding of the cartridge with the plunger driver, for example towards the distal end of the receiving frame.

For automatic operation, in some embodiments, an electric motor is provided to operate the plunger. In order to lower the profile of the device so that it is easy to hold flat and still against the skin, the motor is in some embodiments placed along an axis that is on the same plane as an axis of the cartridge. Optionally, the motor and the cartridge/plunger axes are parallel to each other. Further optionally, both are substantially perpendicular to the axis of injection into the skin, for example, when the cartridge comprises a bent fluid path.

In some embodiments, a cartridge mount is provided in the receiving frame for receiving the cartridge from above. Optionally the cartridge is fixed to the receiving frame after it is lowered into the receiving frame. Alternatively, the cartridge is fixed to the receiving frame while it is being lowered into the receiving frame. As used herein, fixed to the receiving frame relates to restraining the cartridge in place, for example inhibiting its movement for more than 0.1 mm, and/or more than 0.5 mm, and/or more than 1 mm, and/or more than 2 mm, and/or more than 4 mm. In some embodiments, the cartridge mount comprises the interference element with the distal stop, the interference element sized to slidably receive the cartridge and allow the cartridge to slide up to the distal stop.

In some embodiments, a driver mount is provided in the receiving frame for fixedly containing the driver mount. In some embodiments, the driver mount comprises a walled compartment, at least partially surrounding the plunger driver. In some embodiments, the close proximity of the walls of the compartment to the plunger driver causes forces generated in the plunger driver to dissipate, such that forces that might reach the cartridge are reduced.

In some embodiments, the walled containment of the driver mount comprises a gap in its proximal end, sized to accommodate a proximal portion of the driver plunger. Optionally, the gap assists in eliminating mechanical interference when lowering the cartridge with the driver plunger into the receiving frame. In some embodiments, once the cartridge and its associated driver plunger are shifted towards the distal side of the housing, the gap no longer accommodates the driver plunger. Optionally, a housing top cover comprises an extension sized and/or shaped to fit between the gap and the proximal portion of the plunger driver. Optionally, the cover extension serves as an additional supporting wall, aiding in the force dissipation of the driver mount.

In some embodiments, a motor mount is provided in the receiving frame to contain the motor and dissipate forces generated by the motor. In some embodiments, the motor mount comprises an open top for receiving the motor from above. Optionally, the motor mount comprises at least two walls, optionally oppositely positioned, sized to fit over the motor sides, optionally its longitudinal sides. In some embodiments, the walls comprise a rail for slidably guiding and securing the receiving of the motor.

Optionally, the receiving frame is provided with a transmission mount. In some embodiments, the transmission mount is positioned between the motor mount and the plunger driver mount. In some embodiments, the transmission mount comprises an elongated rod configured for fitting with a center of a wheeled transmission system.

In some embodiments, the driver mount and/or the motor mount are suitable for containing forces of at least 10 Kg-cm, or at least 15 Kg-cm, or at least 20 Kg-cm, or at least 25 Kg-cm.

An aspect of some embodiments of the invention relates to force containment between a cartridge having a bent fluid path and an automatic injector apparatus. In some embodiments, force containment comprises reducing movement of a needle of the cartridge with respect to the injector base, which might arise from force exerted on the cartridge, for example, when driving fluid out of the cartridge. In some embodiments, an injector base is provided with a unitary mounting frame having interfering geometry for fitting with the cartridge, optionally at least for fitting with a distal portion of the cartridge and a proximal portion of the cartridge.

In some embodiments, the unitary frame is configured to contain forces along a longitudinal axis of the cartridge. Specifically, in some embodiments, the high forces between the plunger driver system and the plunger are dissipated. Typically, relatively high forces may be exerted on the cartridge by the plunger driving system, for example, about 3-4 Kg. High forces may cause instability of the cartridge which may lead to movement and/or breakage of the cartridge.

Alternatively or additionally, the unitary frame is configured to contain rotational forces. In some embodiments, the cartridge is connected to the needle at an angle, resulting in a configuration which is sensitive to both lateral and rotational movements of the cartridge, where small movements (rotation and/or translation) of the syringe may cause pain to the user or failure of the device. This is as opposed to syringes having a straight needle, which typically are not sensitive to a rotational displacement.

In some embodiments, the unitary frame structure is designed to create a local force balance at cartridge locations prone to impact, for example, at the distal end of the cartridge comprising the needle, where force is exerted when the needle is being pushed into a user's body, and/or at the proximal end comprising the plunger driving assembly, where forces are exerted on the plunger in order to drive fluid out of the cartridge. A potential advantage of using a unitary frame for containing longitudinal force along an axis is the durability of the frame to withstand the forces exerted by the injector operation, potentially reducing breakage and/or disassembly, which might arise in a plurality of interconnected components. Often longitudinal forces are balanced on different parts and/or at different ends of the syringe. For example, proximal plunger driving forces may be absorbed by a door at the proximal end, while a distal force against the cartridge may be absorbed by the injector housing at the front of the injector. This may cause instability of the injector and/or cause high forces on joints between parts.

An aspect of some embodiments of the invention relates to a low profile patch auto injector. In some embodiments a low profile patch auto injector may include a frame fitted to accommodate a cartridge. In some embodiments, the frame is walled. In some embodiments, the frame is pivotly connected at the front, distal end (needle end) of the injector to a base. In some embodiments the injector includes a cover. In some embodiments, the syringe in the cartridge is symmetric. In some embodiments, the syringe in the cartridge is non-symmetric. In some embodiments the frame includes a receiving frame that supports the cartridge.

In some embodiments, at least a portion of the walled frame is floored. In some embodiments, the height of the frame wall varies at different locations. In some embodiments, the wall is continuous throughout its circumference. In some embodiments, the wall is discontinuous in portions of its circumference. In some embodiments, the cover fits over the frame wall. In some embodiments, the cover walls follow and parallel the frame wall. In some embodiments, the cover wall covers missing portions of the frame wall. In some embodiments, the cover includes a removable central section. In some embodiments, the cover central section includes a wall that parallels a portion of the cover wall forming a double wall at that location.

An aspect of some embodiments of the invention relates to a receiving frame that supports the cartridge. In some embodiments, the receiving frame includes a stress containment enclosure. In some embodiments, the stress containment enclosure mechanically mediates stress effected on the frame by the syringe and vice versa. In some embodiments the enclosure includes a portion of the injector cover. In some embodiments, the stress containment enclosure steadies and stabilizes the cartridge. In some embodiments, the receiving frame includes means for supporting the cartridge. In some embodiments, the receiving frame includes coupling mechanisms to attach the cartridge thereto. In some embodiments, the coupling mechanism includes the injector cover. In some embodiments the cartridge includes gripping members. In some embodiments, the receiving frame-cartridge coupling mechanisms function as guides and guide a cartridge being mounted to its correct final location on the receiving frame. In some embodiments the receiving frame supports the injector syringe plunger driving power train.

In some embodiments, the receiving frame supports a printed circuit board (PCB). In some embodiments, the receiving frame supports cover locking/unlocking mechanism. In some embodiments, the receiving frame provides structural support to the frame.

The cartridge may be pre-filled in a sterile aseptic environment using standard equipment for filling syringes prior to insertion in the injector. The injector itself need not be sterile. As the needle is molded into the cartridge it is desirable that the cartridge is immobilized in the injector sufficiently that operating the plunger mechanism to expel the contents does not move the cartridge. If the cartridge were to move then the needle may cause discomfort to the patient in the skin around the needle. In order to provide such immobilization, there may be provided a clip that fits within the injector and which has a catch mechanism for holding the cartridge. The catch mechanism may include bridge holders into which extensions on the body of the cartridge can slide and then be latched at a final resting position by a catch located behind, so that the cartridge can be inserted with a down, slide and click operation.

The injector may provide for insertion of the needle by a simple action of pressing by the user, whether patient or medical personnel when the injector is located on the skin. The needle cover is removed, the injector is placed on the skin and a button is pressed.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Cartridge Immobilization Block Diagram

Referring now to the drawings, FIG. 1 shows a block diagram representing an automatic injector mounting frame for fitting with a cartridge and a driving system of the cartridge, in accordance with some embodiments of the invention.

In some embodiments, an automatic patch injector is mounted on an injection subject. In some embodiments, the automatic injector comprises mounting plate 101. In some embodiments, mounting plate 101 is used for holding the device and for containing the internal components of the injector, such as cartridge 120 having needle 116 at its distal end 104 and plunger 141 at its proximal end 106. In some embodiments, cartridge 120 comprises a reservoir, optionally filled with a pharmaceutical substance. As used herein, a pharmaceutical substance comprises any fluid used for injecting into an injection subject, such as a drug, a placebo, a nutrient and so forth.

In some embodiments, mounting plate 101 comprises receiving frame 110 for fixedly containing at least some of the internal components of the automatic injector. Optionally, receiving frame 110 is unitary, i.e. made from a single piece of material. In some embodiments, receiving frame 110 comprises a ventral side for fixing with mounting plate 101 and/or the injector's base portion, and a dorsal side having geometry for containing internal injector components.

In some embodiments, forces are generated by motor 170 and transmitted to plunger driver 140, optionally through a transmission system. In some embodiments, large forces, for example 3-5 Kg, are generated by plunger driver 140 when driving plunger 141 inside cartridge 120. In order to eliminate forces over the longitudinal axis of the cartridge, which might give in and break, in some embodiments forces are dissipated by receiving frame 110 in proximity to their generation site.

In some embodiments, receiving frame 110 comprises geometries for fixedly containing force generating components and/or force affected components. For example, receiving frame 110 may comprise the driving system of the injector which includes at least a cartridge mount for fixedly receiving cartridge 120, a driver mount for containing plunger driver 140 and a motor mount for containing motor 170. In some embodiments, forces are locally balanced. In some embodiments, receiving frame 110 comprises geometry which contains the components of the driving system of the injector in proximity to one another, for example in proximal end 106. A potential advantage of containing force exerting and exerted components in proximity is that forces may be dissipated close to where they are generated and/or affecting, without being projected to other regions of the injector. Another potential advantage of a limited space for containing force is that force containing structures in receiving frame 110 are provided at the limited region, reducing redundancy of structures.

In some embodiments, receiving frame 110 comprises a platform, e.g. a planer structure. In some embodiments, the components of the driving system, at least cartridge 120, plunger driver 140 and motor 170, are contained side-by-side over the platform, optionally each of the components are placed along their longitudinal axis. In some embodiments, the longitudinal axes of cartridge 120, plunger driver 140 and motor 170 are positioned on the same plane, and/or parallel planes, optionally additionally parallel to the injector base plane. A potential advantage of placing the longitudinal axes laterally on substantially the same plane is limiting the height of the housing and injector device, possibly making it easier to be held by hand, and easier to transport.

High Level Overview of Cartridge Immobilization

Reference is now made to FIG. 2, showing a high level overview of a method for immobilizing movement of a cartridge with respect to an automatic injector housing, in accordance with some embodiments of the invention.

In some embodiments, a housing is provided 202 having within it a receiving frame. In some embodiments, the receiving frame serves as a chassis, containing the internal components of the injector. In some embodiments, a cartridge is lowered 204 into the receiving frame fitted within the housing from above. Optionally, the cartridge is lowered while being mechanically coupled to a plunger driver. In some embodiments, mechanical coupling between the cartridge and the plunger driver comprises an arm, optionally telescopically extended, which mechanically connects to a plunger residing within the reservoir of the cartridge. Alternatively or additionally, the cartridge may be lowered into the receiving frame while being mechanically coupled to a motor, the motor being in operable mechanical communication with the plunger driver, optionally through a transmission system.

In some embodiments, the cartridge, and possibly its associated components, is being laterally moved by sliding 206 towards the distal end of the receiving frame, defined as the end fitting with the distal portion of the cartridge, which comprises the needle outlet. In some embodiments, by sliding the cartridge in 206, the cartridge is interlocked 208 with the receiving frame, optionally by engaging with geometry provided in the receiving frame, such as interference elements and/or snap latches. A potential advantage of activating engagement by positional translocation into a fitting geometry is that it enables a delicate interlocking mechanism, i.e. a mechanism which requires a small amount of force to apply, as opposed to a mechanism of elastic fitting which operates on the basis of first pushing away the interfering element, instead of sliding into it.

In some embodiments, the cartridge is lowered down from above while being mechanically coupled with the driving system of the injector, e.g. the plunger driver and/or the motor. In some embodiments, the receiving frame contains walled compartments for receiving the coupled components of the cartridge. In some embodiments, the walled compartments are not uniform in wall height, for example having gaps, and enable some portions of the driving system to extend beyond the boundaries of the walled compartments. Optionally, by sliding 206 the cartridge into its interlocked position, the driving system components extending beyond the boundaries are shifted to be positioned as a whole inside the boundaries of the walled compartments. In some embodiments, a space is formed between the wall having the gap and the driving system components.

Optionally, the receiving frame is covered 210 with a housing cover. In some embodiments, the housing cover complements gapped regions in the walled compartments of the receiving frame. In some embodiments, the housing cover comprises extensions sized and/or shaped for fitting in the space between the wall and the shifted component. In some embodiments, the filling in of the extension provides mechanical support for the components, aiding in the dissipation of the force emanating from the components. For example, being mechanically connected to the plunger, the plunger driver may be found in a proximal position to the cartridge. A gap in the walled compartment containing the plunger driver enables the proximal portion of the plunger driver to extend beyond the boundary of the wall. When the cartridge is shifted distally by sliding, so does the coupled plunger driver. By shifting distally, the plunger driver may now be fully contained within the compartment.

However, the remaining gap may lead to insufficient containment of forces which cause the plunger driver to shift towards a proximal direction. Filling this space with the cover, may provide a supporting wall that would balance these forces, reducing movement of the plunger driver. In some embodiments, the plunger driver delivers 212 fluid by extending a threaded telescopic extension towards the distal direction, where the plunger is with respect to the plunger driver. The plunger is then pushed towards the distally located outlet comprising the needle, driving the fluid out of the cartridge. Providing the proximal support in the form of the walled compartment, provides an anchoring point enables the extending arm to push the plunger distally, against the pressure of the fluid, rather than having the plunger driver being pushed proximally.

Exemplary Unitary Mounting Frame

Reference is now made to FIG. 3A, illustrating an exemplary unitary mounting frame illustrating a distal and proximal geometry for fitting with and immobilizing components of an injector, in accordance with some embodiments of the invention.

In some embodiments, receiving frame 110 comprises two regions of geometric fitting, a proximal region and a distal region. In some embodiments, a distal region secures the distal portion of cartridge 120 by distal mount 325, exemplified and illustrated, for example in FIG. 4, showing the distal mounting pin 422 of cartridge 120 and FIG. 10 showing the distal mount engaged with the distal mounting pin 422 of cartridge 120. In some embodiments, a proximal region of receiving frame 110 comprises the proximal force generating components of the injector. In some embodiments, the two regions are positioned on floor 111 of receiving frame, which is optionally not continuous between the regions, as exemplified and shown in FIG. 10. In some embodiments, floor 111 is substantially flat and serves as a base on which the complementary geometries of receiving frame 110.

In some embodiments, a proximal portion of receiving frame comprises a cartridge mount 327, a plunger driver mount 315 and a motor mount 317. Optionally, all mounts are found in proximity to one another, potentially dissipating forces near their generation sites and reducing forces propagation into less secured components and regions. In some embodiments, each mount contains geometric features which are sized and shaped to contain the injector components. Optionally, the receiving frame and its geometric features are unitary, for example, by generating them in a molding process. In some embodiments, the mounts comprise joint walls and/or geometries for containing forces from both sides of the mounts.

In some embodiments, cartridge mount 327 comprises complementary geometry for fitting with geometric structures in the proximal end of cartridge 120. For example, interference elements 332, distal stop 333 and snaps 334, which are further exemplified and illustrated in FIGS. 6, 8A, 8B, 9 and 10.

In some embodiments, driver mount 315 comprises walls 316 defining a containing compartment, optionally covering at least a portion of three sides of the plunger driver. In some embodiments, a forth side of the plunger driver is secured by being mechanically coupled to cartridge 120. Potentially, the walls stabilize the forces generated by plunger driver 140 and prevent its movement in at least three directions. It is a potential advantage to immobilize the plunger driver when it is mechanically coupled to the cartridge, in order to reduce movement which would result in movement of the cartridge. In addition, dissipating forces close to their generating sites reduces the effect of these forces at other sites.

In some embodiments, driver mount 317 is open topped, allowing for the plunger driver to be loaded from above. In some embodiments, due to its coupling to cartridge 120, and since cartridge 120 is distally shifted, the geometry of driver mount 317 permits a distal translocation of plunger driver 140, for example, by providing a walled compartment which is bigger than the distal-proximal axis of plunger driver 140. In some embodiments, a space formed between the proximal wall and the proximal end of driver 140 is filled by an extension of the housing cover, optionally sized and/or shaped for fitting into the formed to space. In some embodiments, gap 320 is provided to allow for a more proximal positioning of driver 140, without mechanical interference by the proximal wall. Gap 320 is further shown and illustrated in FIG. 3B and FIG. 9.

In some embodiments, a motor mount 317 is provided, optionally in proximity to the proximal end of the cartridge which is relatively secured. In some embodiments, motor mount is positioned laterally with respect to driver mount 315. In some embodiments, motor mount comprises walls 318 fitting the width of motor 170. Optionally, walls 318 comprise guiding rails 319, guiding an insertion of motor 170 into its mount 317. In some embodiments, walls 318 are not continuous and provide access for a transmission system to interconnect between the motor 170 and plunger driver 140.

Exemplary Unitary Mounting Frame Fitted with Various Components of an Automatic Injector Reference is now made to FIG. 3B, an exemplary unitary mounting frame fitted with some components of an automatic injector, in accordance with some embodiments of the invention.

In some embodiments, an automatic injector device includes an actuator, for example motor 170, optionally DC motor. In some embodiments, an automatic injector device includes transmission 302, for example mechanically coupled to a plunger driver 140. In some embodiments, an automatic injector device includes a power source. When the power source is electrically connected to motor 170, motor 170 optionally rotates gear wheels of transmission 302 being attached to driving plunger 141 to discharge a drug.

Optionally a cartridge 120 may be installed into the device (for example preinstalled and/or installed by a user). In some embodiments the cartridge may include reservoir 410 optionally containing a drug and/or plugged at a proximal location with a plunger seal 140 and/or having an extension 305 and/or needle 116, optionally protected by a needle cap (not shown). Optionally plunger driver 140 may also be a part of cartridge 120. Alternatively or additionally plunger driver 140 may be part of the injector device.

In some embodiments, receiving frame 110 further comprises an electric motor 170 for operating plunger 141 to empty the reservoir 410 into needle 116, optionally to inject fluid from the reservoir 410 into the injection subject. In some embodiments, the motor and the reservoir have parallel longitudinal axes, optionally typically perpendicular to the axis of the needle at the point of injection. In some embodiments, motor 170 is held to receiving frame 110 by mountings 318 and operates transmission 302, optionally having a succession of gear wheels, to advance plunger 141.

Exemplary Cartridge

Reference is now made to FIG. 4, illustrating an exemplary cartridge having distal and proximal mounting pins for connecting with a mounting frame, in accordance with some embodiments of the invention.

In some embodiments, the automatic injector cartridge comprises complementary geometry for fitting with the geometry provided in receiving frame 110. For example, the proximal end of cartridge 120 comprises mounting pins 425, which may engage with cavities 332 in receiving frame 110. In some embodiments, mounting pins 425 extend beyond the outer boundary of the body of reservoir 410. Optionally, mounting pins 425 are connected through pin connection 427, which may be for example an extended rod connecting between the pins and potentially providing greater stability and strength than pins which are unrelated to one another. In some embodiments, mounting pins 425, and optionally connection 427, together with their complementary geometry in the receiving frame, determine the directionality of insertion of cartridge 120 into the injector. It is a potential advantage to provide directionality indicators such as pins 425, when using an off-centered fluid outlet, and/or when using a bent fluid path, both defining a preferable orientation with respect to an injection subject.

In some embodiments, a distal complementary geometry is provided at the distal end of cartridge 120. For example, distal mounting pin 422 is provided as an extension protruding from the distal boundary of the cartridge, optionally centered. In some embodiments, pin 422 is sized to fit with fitting geometry on the proximal end of receiving frame 110.

In some embodiments, both pins 425 and pin 422 are shaped to engage with cavities which are positioned distally to the pins. This directionality enables the loading of the cartridge by sliding it towards the distal cavities until reaching a mechanical stop. For example, until pins 425 run into distal stop 333, and/or until pin 422 is fully inserted into cavity 325 and the cartridge distal wall mechanically inhibits further movement. Optionally, mounting pins 425 are proximally secured by snaps which elastically deflect to allow lowering the cartridge, and snap back into position when the mounting pins 425 are slid distally.

Exemplary Cartridge Loading into an Injector and Fitting with a Unitary Mounting Frame Reference is now made to FIG. 5, illustrating an explosive view of an automatic injector being loaded with a cartridge and covered with a cover, in accordance with some embodiments of the invention.

In some embodiments, the injector has a base part 520 which is placed in contact with the skin of a subject to receive the injection. In some embodiments, receiving frame 110 receives and fixes cartridge 120 within mounting plate 101. The mounting plate 101 is pivotally mounted on base 520.

In some embodiments, receiving frame 110 comprises an interference element 332 with a distal stop 333 and optionally snap, for example elastic snap lock 334. The cartridge is lowered vertically into the slide connecter, pushing down snap 334. The cartridge is then slid forward to the distal stop and upon reaching the distal stop the latch is released to latch the cartridge in place from behind against the distal stop. The down, slide, click motion of inserting the cartridge into receiving frame 110 is illustrated by arrows A and B, illustrating the downwards loading and the lateral sliding towards the distal end, respectively.

In some embodiments, cover 510 fits on mounting plate 101 over the reservoir part of the cartridge 120, after the cartridge is placed in position, optionally having extensions, for example extension 512, for filling in the space which is formed between plunger driver 140 and receiving frame 110.

Exemplary Geometry and Interference Connection

Reference is now made to FIG. 6, illustrating a close-up cross-sectional view of an exemplary geometry and interference connection of a proximal portion of a unitary mounting frame with a proximal portion of a cartridge, in accordance with some embodiments of the invention.

Illustrated is a perspective view of an exemplary proximal connector structure, showing interference elements and snaps for mounting a cartridge to a receiving frame. Optionally snaps and/or fittings and/or pins may be molded into the cartridge. For example fittings may include a plastic snap, a rivet, a pin, a cut out, an indentation, a protuberance, snap clamps, a catch, a ball fitting, a latch, a barb etc.

In some embodiments, two interference elements are provided, for example interference elements 332. It should be noted that the view illustrated in FIG. 6 shows only one interference element 332, but another one is found on the opposite side not shown in this view. This is applicable to all other components which are mentioned herein to include two members, but showing only one, unless mentioned otherwise.

In some embodiments, interference elements 332 are shaped to have a cavity shape by covering three sides of pins 425. For example, the bottom side is covered by the receiving frame's floor 111, optionally in an offset position to the fitting from other directions, as in some embodiments, the mounting pin 425 extends along the entire length of the cartridge proximal side through connection 427, as shown in FIG. 4. The top side is, for example, covered by an overhanging portion of interference elements 332 which overhangs mounting pin 425. The distal side of the mounting pin 425 is, for example, covered with distal stop 333, which in some embodiments comprised of a distal mechanically interfering wall, optionally part of interfering element 332.

In some embodiments, for example, two snaps 334 latch to pins 425 to hold the proximal end of cartridge 120 to a receiving frame 110. Optionally latches 334 are flexible plastic. As cartridge 120 is lowered onto receiving frame 110, pins 425, for example see FIG. 5, pushes latches 334 downwards, for example by elastically bending plastic latches 334. Once cartridge 120 is in place, latches 334 snap back to secure pins 425 from their proximal side. Alternatively or additionally, latches 334 may be made of spring steel and/or may be rigid and held by a pivot and/or spring etc.

Illustrated in FIG. 6 is an exemplary telescoping plunger driver 140. For example, plunger driver may include threaded telescoping rods such that when a transmission is rotated (for example by a motor) the telescoping rods expand driving plunger seal 141 into reservoir 410 and/or discharging the pharmaceutical substance out of fluid path 305.

Also illustrated in FIG. 6 are driver mount 315, having containing walls for containing plunger driver 140, and having gap 320 and space 620, which is formed in some embodiments between plunger driver 140 and the proximal wall of driver mount 315, and is optionally filled with cover extension 512.

Exemplary Planar Configuration

Reference is now made to FIG. 7, illustrating a perspective top view of an exemplary side-by-side configuration of the cartridge and the driving system of the cartridge, in accordance with some embodiments of the invention.

In some embodiments, cartridge 120, plunger driver 140 and motor 170 are provided side by side on top of receiving frame 110, potentially reducing the height of the injector, potentially leading to an injector being held more easily by an injection subject and/or a caregiver. In some embodiments, the components are arranged in proximity to one another, potentially dissipating forces in proximity to their generation site by the containing structure of receiving frame 110.

Exemplary Cartridge Proximal Fitting

Figure 8B:
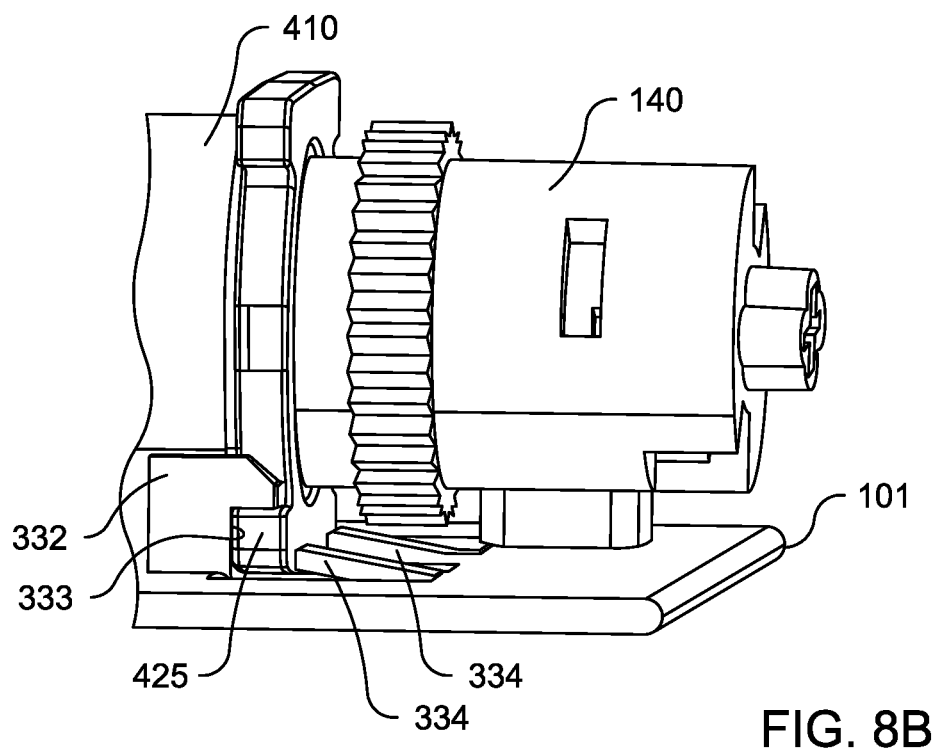

Reference is now made to FIGS. 8A and 8B, illustrating a side view of a snap fitting and immobilization of a cartridge, in accordance with some embodiments of the invention, wherein FIG. 8A illustrates a cross-sectional view of FIG. 8B illustrates a partial perspective view.

FIG. 8A illustrates a wide view of a side cross-section of the receiving frame 110, mounted with cartridge 120. Illustrated are distal mount 325 and proximal mounting assembly, comprising interference elements 332 and snaps 334. In some embodiments, the containing compartment 315 of plunger driver is positioned in proximity to the proximal end of cartridge 120.

FIG. 8B illustrates the proximal mechanical proximity of cartridge 120 with plunger driver 140, when they are mechanically coupled through plunger 141 residing in reservoir 410. Also shown in FIG. 8B is the proximity of the proximal fitting assembly of cartridge 120 with receiving frame 110, comprising for example mounting pins 425 surrounded by interference elements 332, distal stop 333 and snaps 334. A potential advantage of providing a securing assembly such as the proximal fitting assembly in proximity to the plunger driver is by dissipating the forces near their generation site where they affect the most, and potentially reducing the propagation of the forces into less secured or sturdy regions of the cartridge.

Exemplary Incorporation of a Cover Extension

Reference is now made to FIG. 9, illustrating a cross-sectional side view of the automatic injector, illustrating an incorporation of a cover extension in the immobilization system, in accordance with some embodiments of the invention.

In some embodiments, gap 320 is utilized for receiving the proximal end of plunger driver 140 before it is shifted distally by sliding being mechanically coupled to cartridge 120, through plunger 141. Shown in FIG. 9 is gap filling by extension 512 of cover 510. In some embodiments, extension 512 provides mechanical contra for the force exerted by the proximal portion of plunger driver 140, which results from extending the threaded telescoping rod system of plunger driver 140. In some embodiments, extension 512 prevents plunger driver 140 from shifting in a proximal direction, and enables plunger 141 to be pushed in a distal direction.

Exemplary Cartridge Distal Fitting

Reference is now made to FIG. 10, illustrating a bottom perspective view of an exemplary unitary mounting frame, showing a distal fitting with a cartridge, in accordance with some embodiments of the invention.

In some embodiments, a frame floor 111 serves as a base structure of receiving frame 110, and giving mechanical support for the complementary and/or containing geometry of receiving frame 110, and also connecting between the geometrical features. FIG. 10 shows a bottom view of the geometrical features as positioned on floor 111.

Shown in FIG. 10, for example, is distal mounting pin 422 fitted with distal mount 325. In some embodiments, distal mount 325 comprises a cavity sized for insertion of pin 422. Optionally, distal mount 325 covers at least the top portion of pin 422, potentially balancing mechanical forces reaching from the ventral direction from inserting the needle 116 into an injection subject. In some embodiments, distal mount 325 also secures cartridge 120 by mechanically inhibiting further distal movement of the cartridge with respect to receiving frame 110.

Also shown in FIG. 10 is a bottom view of snaps 334. In some embodiments, the floor 111 of receiving frame 110 is continuous at least between the proximal end of the driving system and the distal end of the cartridge, serving as a wide mechanical platform base. Alternatively, and as exemplified in FIG. 10, floor 111 is not continuous and comprises apertures. Optionally, at least the proximal end and/or at least the distal end include continuous regions of floor 111. A potential advantage of splitting the continuous regions is that each region would contain forces generated in proximity to it, and the forces would propagate less to other regions.

Exemplary Dimensions of a Drug Delivery Device

In some embodiments the payload of a reservoir (for example a syringe) may include, for example between 0.5 and 2 ml and/or between 2 and 4 ml and/or between 4 and 6 ml and/or between 4 and 10 ml of a drug and/or more. In some embodiments, the injector may discharge the entire payload as a single dose. A drug delivery device may include, for example, a patch injector, and/or an internally powered driver to drive the plunger and/or discharge the payload. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or between 600 seconds and an hour and/or between an hour and a day and/or longer.

In general, discharge may be driven by a driver. An internally powered driver may be powered by various mechanisms including for example a motor as discussed, including for example a DC motor, an actuator, a brushless motor, and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the present invention may include a reservoir part as discussed. For example a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe barrel. For example, the hollow of the needle may be in fluid communication with the interior of the barrel.

The needle may optionally be rigidly attached to the extension at the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. In some embodiments a plunger may slide axially along the inside of the barrel to discharge a medicine payload. For example, the medicine may be discharged through the hollow needle. The protruding tip of the needle may be oriented at an angle to the axis of the barrel.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example the mechanism may include a snap that gives way at 40 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N-cm. The trigger torque (the torque at which the needle safeguarding is triggered) may range for example between to 0.5 to 2 and/or from 2 to 4 and/or from 4 to 10 N-cm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments the reservoir may have a length ranging for example between 20 and 42 and/or 42 and 48 mm and/or 48 and 80 mm and/or 80 and 200 mm. In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a reservoir may have a circular cross section such that width is the diameter of the circle. In some embodiments an extension may have a straight end portion with a length ranging for example between 1 and 3 mm or 3 and 7 mm or 7 and 8 or 8 and 10 mm or 10 and 15 mm or 15 and 50 mm. In some embodiments the exposed straight portion of a needle may have a length ranging for example between 1 and 5 mm or 5 and 7 mm or 7 and 10 mm or 10 and 20 mm.

For a non-uniform cross section an average outer width may be defined as the width of the smallest oval that can enclose the neck averaged over the length of the neck. In some embodiments a fluid path between the extension and a reservoir cavity may include a 27 gauge needle or a needle ranging between 25 and 30 gauge or a needle ranging between 20 and 25 gauge or a needle ranging between 30 and 32 gauge. In some embodiments a needle protruding from an extension may include a 27 gauge needle or a needle ranging between 25 and 30 gauge or a needle ranging between 20 and 25 gauge or a needle ranging between 30 and 32 gauge.

General

As used herein the term "about" refers to ±25%.

The terms "comprises", "comprising", "includes", "including", "having" and their conjugates mean "including but not limited to".

The term "consisting of means" "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A receiving frame for immobilizing a cartridge to an automatic injector housing, the cartridge including a connection feature and a needle at a distal end of said cartridge, the cartridge being mechanically coupled at a proximal end of said cartridge to a plunger driver, the receiving frame comprising:
    a ventral side configured to fit into a base portion of said automatic injector housing; and
    a dorsal side including:
        a cartridge mount configured to receive said cartridge from a first direction perpendicular to a longitudinal axis of the receiving frame, the cartridge mount configured to latch the cartridge in place after said cartridge is received from the first direction and slide in a second direction parallel to the longitudinal axis of the receiving frame, said cartridge mount comprising:
            an interference element with a distal stop, wherein the interference element is sized to slidably link to said connection feature and allow said cartridge to slide in the second direction up to said distal stop; and
            a snap element that allows the interference element to receive the connection feature, wherein the snap element is configured to inhibit disconnection of said cartridge from said interference element after the cartridge is received in the first direction, slid in the second direction, and latched in place; and
        a driver mount configured to fixedly contain said plunger driver, said driver mount comprising a walled container sized to at least partially surround said plunger driver and defining an open top for receiving said plunger driver,
    wherein said cartridge and said driver mount are configured to be mechanically coupled through said plunger driver.

2. The receiving frame of claim 1, further comprising a motor mount, configured to fixedly contain a motor in operable communication with the plunger driver, said motor mount comprising a walled container sized to at least partially surround said motor and defining an open top for receiving said motor.

3. The receiving frame of claim 2, wherein said cartridge mount, said driver mount, and said motor mount are a unitary piece.

4. The receiving frame of claim 2, wherein a longitudinal axes of each of said cartridge, said plunger driver, and said motor are configured to be positioned on a same plane.

5. The receiving frame of claim 1, wherein said driver mount contains forces of at least 20 kg-cm.

6. The receiving frame of claim 1, wherein said interference element is shaped to surround a portion of said cartridge from a dorsal, a distal, and a ventral side of said portion of said cartridge.

7. The receiving frame of claim 1, wherein the snap element is configured to elastically deflect during slidable engagement of the connection feature of the cartridge with the interference element of the cartridge mount and to subsequently release to snap back, immobilize and inhibit disconnection of the cartridge from the cartridge mount.

8. The receiving frame of claim 1, wherein the interference element is sized to allow said cartridge to slide up to said distal stop along the second direction, and the distal stop and the snap element are together configured to inhibit movement of the connection feature of the cartridge along the second direction.

9. The receiving frame of claim 8, wherein the snap element is configured to elastically deflect during sliding of the cartridge within the interference element in the second direction and to subsequently release to snap back and immobilize disconnection of the cartridge from the interference element.

10. The receiving frame of claim 1, wherein the snap element is elastic.

\* \* \* \* \*